United States Patent
Lub et al.

(10) Patent No.: US 9,825,241 B2
(45) Date of Patent: Nov. 21, 2017

(54) GREEN EMITTING PHOSPHORS COMBINED WITH BROAD BAND ORGANIC RED EMITTERS WITH A SHARP NEAR IR CUT OFF

(71) Applicant: PHILIPS LIGHTING HOLDING B.V., Eindhoven (NL)

(72) Inventors: Johan Lub, Valkenswaard (NL); Rifat Ata Mustafa Hikmet, Eindhoven (NL); Ties Van Bommel, Horst (NL)

(73) Assignee: PHILIPS LIGHTING HOLDING B.V., Eindhoven (NL)

(*) Notice: Subject to any disclaimer, the term of this patent is extended or adjusted under 35 U.S.C. 154(b) by 0 days.

(21) Appl. No.: 14/766,900

(22) PCT Filed: Jan. 26, 2014

(86) PCT No.: PCT/IB2014/058547
§ 371 (c)(1),
(2) Date: Aug. 10, 2015

(87) PCT Pub. No.: WO2014/122549
PCT Pub. Date: Aug. 14, 2014

(65) Prior Publication Data
US 2015/0372240 A1 Dec. 24, 2015

Related U.S. Application Data

(60) Provisional application No. 61/763,025, filed on Feb. 11, 2013.

(30) Foreign Application Priority Data

Jul. 4, 2013 (EP) .................... 13175123

(51) Int. Cl.
C08G 73/06 (2006.01)
H01L 51/00 (2006.01)
(Continued)

(52) U.S. Cl.
CPC ........ *H01L 51/0072* (2013.01); *C07D 471/06* (2013.01); *C09K 11/025* (2013.01);
(Continued)

(58) Field of Classification Search
CPC ........ C09K 2211/14; C09K 2211/1466; C09K 2211/1018; C09K 11/08; H05B 33/14; F21V 9/16; H01L 51/00; H01L 51/0053
See application file for complete search history.

(56) References Cited

U.S. PATENT DOCUMENTS 4,845,223 A 7/1989 Seybold et al.
5,122,306 A * 6/1992 Van Moer ............ C09K 11/07
252/582

(Continued)

FOREIGN PATENT DOCUMENTS

WO WO2010116294 A1 10/2010
WO WO201204234 A1 4/2012
(Continued)

OTHER PUBLICATIONS

Chen et al. (Chem. Eur. J. 2007, 13, 450-465).*

*Primary Examiner* — Shane Fang

(57) ABSTRACT

The invention provides a lighting device (1) comprising (a) a light source (10) configured to generate light source light (11), and (b) a light converter (100) configured to convert at least part of the light source light (11) into visible converter light (111), wherein the light converter (100) comprises a matrix (120) containing an organic luminescent material (140) of the perylene type. The lighting device may further comprise an inorganic luminescent material (130).

12 Claims, 10 Drawing Sheets

(51) Int. Cl.
  *C09K 11/06*   (2006.01)
  *C09K 11/77*   (2006.01)
  *H01L 51/50*   (2006.01)
  *H05B 33/14*   (2006.01)
  *C07D 471/06*   (2006.01)
  *C09K 11/02*   (2006.01)
  *H01L 51/52*   (2006.01)
  *H05B 33/12*   (2006.01)
  *F21K 9/64*   (2016.01)
  *F21Y 115/10*   (2016.01)

(52) U.S. Cl.
  CPC .......... *C09K 11/06* (2013.01); *C09K 11/7729* (2013.01); *H01L 51/0053* (2013.01); *H01L 51/502* (2013.01); *H01L 51/5262* (2013.01); *H05B 33/12* (2013.01); *H05B 33/14* (2013.01); *C09K 2211/1007* (2013.01); *C09K 2211/1044* (2013.01); *F21K 9/64* (2016.08); *F21Y 2115/10* (2016.08); *H01L 51/5016* (2013.01); *H01L 51/5036* (2013.01); *H01L 2251/303* (2013.01)

(56) References Cited

U.S. PATENT DOCUMENTS

| | | | |
|---|---|---|---|
| 2003/0111649 | A1 | 6/2003 | Park et al. |
| 2010/0033947 | A1* | 2/2010 | Lin .................. G02F 1/133603 362/84 |
| 2010/0289044 | A1 | 11/2010 | Krames et al. |

FOREIGN PATENT DOCUMENTS

| | | |
|---|---|---|
| WO | WO2012042438 A1 | 4/2012 |
| WO | WO2012113884 A1 | 8/2012 |

* cited by examiner (68)

(17)

(65)

(53)

(2)

(52)

(63)

(64)

(X1)

(X2)

GREEN EMITTING PHOSPHORS COMBINED WITH BROAD BAND ORGANIC RED EMITTERS WITH A SHARP NEAR IR CUT OFF

CROSS-REFERENCE TO PRIOR APPLICATIONS

This application is the U.S. National Phase application under 35 U.S.C. §371 of International Application No. PCT/IB14/058547, filed on Jan. 26, 2014, which claims the benefit of U.S. Provisional Patent Application No. 61/763,025, filed Feb. 11, 2013, and European Patent Application No. 13175123.2 filed on Jul. 4, 2013. These applications are hereby incorporated by reference herein.

FIELD OF THE INVENTION

The invention relates to a lighting device comprising (a) a light source configured to generate light source light, and (b) a light converter configured to convert at least part of the light source light into visible converter light. The invention further pertains to such light converter per as well as to an organic luminescent material that can comprised by such light converter.

BACKGROUND OF THE INVENTION

Phosphor-enhanced light sources are known per se and are used for substantially all kinds of light sources. Phosphor-enhanced light sources comprise a light emitter and a luminescent material. The luminescent material is arranged for converting at least part of the light emitted by the light emitter into light of a longer wavelength.

Well-known phosphor-enhanced light sources are, for example, mercury vapor discharge lamps in which the light is emitted from a discharge in which the presence of mercury vapor causes the discharge to emit ultraviolet radiation. At least a part of the ultraviolet radiation is absorbed by a luminescent material and converted into light of a longer wavelength which is subsequently emitted by the luminescent material. Such mercury vapor discharge lamp may, for example, comprise a discharge vessel in which the discharge is generated. The luminescent material is typically applied to the inner wall of the discharge vessel such that the ultraviolet radiation emitted by the discharge does not need to pass the discharge vessel but is inside the discharge vessel converted into, for example, visible light.

Alternatively, the phosphor-enhanced light source may comprise a solid-state light emitter as the light emitter. Such a solid-state light emitter may, for example, be a light emitting diode, or a laser diode, or an organic light emitting diode. The light emitted by a solid-state light emitter typically has a relatively narrow spectrum arranged around a center wavelength. The width of the spectrum may, for example, be defined by the Full Width Half Maximum (further also indicated as FWHM) of the emission peak which is a width of the emission peak measured at an intensity being half the maximum emission intensity of the light emitted by the solid-state light emitter. The FWHM of a typical emission spectrum of the solid-state light emitter is less than 30 nanometer, which is typically identified by the human eye as light of a single color.

To change the color of the light emitted by the solid-state light emitter, luminescent materials may be added to generate a phosphor-enhanced light source. The luminescent material may, for example, be applied as a layer on top of the (LED) die of the solid-state light emitter, or may, for example, be dispersed in a matrix which may be located at a distance of the solid-state light emitter, a so called "remote phosphor" arrangement. The luminescent material may also be part of a mixture of different luminescent materials, for example, each generating a different color such that the mixed light, for example, generates white light having a specific color temperature. Furthermore, luminescent materials may be added to solid-state light emitters to improve the color rendering characteristics of the solid-state light emitters, as the typical emission characteristic of the luminescent materials is a relatively broad spectrum of light.

Recently new luminescent materials are being used in phosphor-enhanced light sources, such as organic luminescent materials, especially to replace known inorganic luminescent materials which are used to provide the "Red"-contribution in white light sources. WO2011/116294 describes for instance such luminescent materials.

SUMMARY OF THE INVENTION

Efficiency of white emitting light solid state light sources can still be improved. This can be best done by combining RGB LEDs. However, green LEDs are presently not efficient enough in order to obtain high efficiencies. For this reason, phosphor converted (PC) LEDs are suggested for obtaining white light. However, currently used phosphors, such as YAG:Ce, may emit too far into far red which decrease the efficacy as the human eye is not sensitive to the far red.

Hence, it is an aspect of the invention to provide an alternative lighting device, and especially an alternative light converter, which preferably further at least partly obviate one or more of above-described drawbacks. It is further an aspect of the invention to provide an alternative red luminescent material and/or a combination of a green luminescent material and such red luminescent material, which preferably further at least partly obviate one or more of above-described drawbacks.

Here, we suggest using "green" emitting phosphors, especially with a cutoff equal to or below 600 nm (such as especially having a spectral distribution with at least 70% of the energy below 600 nm), combined with an organic phosphor with a cutoff in the red tail, especially with a cutoff equal to or below 650 nm, even more especially equal to or below 620 nm. Preferentially, the green and red emitting phosphors are in the remote phosphor configuration which may lead to a total increase in the system efficacy. This configuration is most suitable in low power low operating temperature applications such as TLED (tube LED configuration, e.g. LEDs implement in a T8 tube (known in the art of fluorescent lighting)). Many of the herein suggested luminescent materials have a fraction of emission light energy below 645 nm of 0.8 or higher, under 450 nm excitation.

In a first aspect, the invention provides a lighting device comprising (a) a light source configured to generate light source light, (b) a light converter configured to convert at least part of the light source light into visible converter light, wherein the light converter comprises a matrix containing an organic luminescent material as defined by formula (I) (wherein the organic luminescent material is especially configured to provide red light, even more especially red light with a spectral distribution with at least 70% of the energy below 650 nm (sharp near IR cut off)) (especially under 450 nm excitation), and (c) optionally an inorganic luminescent material (especially configured to provide at least green light), with the organic luminescent material according to formula (I):

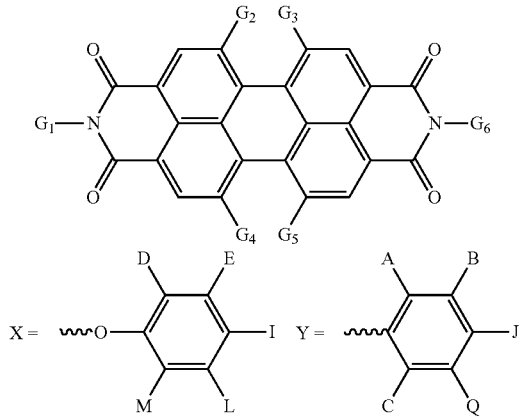

in which:

G₁ and G₆ independently comprise a group selected from a linear alkyl, a branched alkyl, an oxygen-containing alkyl, a cycloalkyl, a naphtyl, and Y;
  wherein each of A, B, C, J and Q independently comprise a group selected from hydrogen, fluorine, chlorine, isopropyl, t-butyl, methoxy, an alkyl with up to 16 carbon atoms, and an oxygen containing alkyl with up to 16 carbon atoms;
G₂, G₃, G₄ and G₅ independently comprise a group selected from hydrogen, fluorine, chorine, isopropyl, t-butyl, methoxy, alkyl with up to 16 carbon atoms, and oxygen-containing alkyl with up to 16 carbon atoms, and X;
  wherein each of D, E, I, L and M independently comprise a group selected from hydrogen, fluorine, chlorine, isopropyl, t-butyl, methoxy, alkyl with up to 16 carbon atoms, and an oxygen-containing alkyl with up to 16 carbon atoms; and in which (in a specific embodiment) at least two selected from G2, G3, G4, and G5 at least comprise X, wherein (in a specific embodiment) independently at least one of D, E, I, L and M of at least two of said at least two selected from G2, G3, G4, and G5 comprise a group selected from fluorine and chlorine, especially fluorine.

Especially, at least two of said at least two selected from G2, G3, G4, and G5 comprise two or more groups selected from fluorine and chlorine, especially fluorine. However, chlorine groups appear to provide good results as well. Desired optical properties may especially be obtained when all G2-G5 at least comprise X (and at least two, especially all four, comprise a fluorine substituent). Hence, in an embodiment G2-G5 are each independently X.

The linear alkyl, branched alkyl, oxygen containing alkyl (see also below), cycloalkyl, and the naphtyl, as defined above for especially G1 and G6, may especially comprise up to 44 carbon atoms. The alkyl (or naphtyl) may also be substituted with fluorine. In an embodiment, G1 and G6 are each independently $C_nH_{2n+1-m}F_m$ with n≤44, and m≤2n+1. Other substituents are not excluded. Especially, the alkyl comprises up to 20, such as up to 10, like up to 8 carbon atoms.

The oxygen containing alkyl, with especially up to 44 carbon atoms, as defined above for especially G1 and G6, may in an embodiment especially relate to $C_nH_{2n+1}O_m$, with n being an integer from 1 to 44 and m<n/2. The oxygen containing alkyl, with especially up to 44 carbon atoms, may also be substituted with fluorine. Other substituents are not excluded. The oxygen containing alkyl may be linear, branched, or cyclic, or may be a combination of two or more thereof. The oxygen containing alkyl especially comprises an alcohol or an ether, such as an oligo ethylene oxide. Especially, n is up to 20, such as up to 10, like up to 8.

G1 and G6 may be the same or may be different (see also below).

The alkyl with up to 16 carbon atoms, as defined above for A, B, C, J, Q, G2, G3, G4 and G5, D, E, I, L and M, especially relate to $C_nH_{2n+1}$, with n being an integer from 1 to 16. The alkyl may be linear, branched, or cyclic, or may be a combination of two or more thereof. The alkyl with up to 16 carbon atoms may also be substituted with fluorine (see below). Other substituents are not excluded. Especially, the alkyl comprises up to 10, such as up to 8 carbon atoms.

The oxygen containing alkyl with up to 16 carbon atoms, as defined above for A, B, C, J, Q, G2, G3, G4 and G5, D, E, I, L and M, especially relates to $C_nH_{2n+1}O_m$, with n being an integer from 1 to 16 and with m≤n/2. The alkyl may be linear, branched, or cyclic, or may be a combination of two or more thereof. The oxygen containing alkyl with up to 16 carbon atoms may also be substituted with fluorine (see below). Other substituents are not excluded. Especially, n is up to 10, such as up to 8.

Hence, in an embodiment, the alkyl with up to 16 carbon atoms may at least partially be substituted with fluorine, and may in an embodiment especially relate to $C_nH_{2n+1-m}F_m$ with n being an integer from 1 to 16 and with m≤2n+1. The fluorine substituted alkyl may be linear, branched, or cyclic, or may be a combination of two or more thereof. Other substituents are not excluded. Especially, n is up to 10, such as up to 8.

A, B, C, J, Q may independently be chosen. G2, G3, G4 and G5 may independently be chosen. D, E, I, L and M may independently be chosen.

In a further aspect, the invention also provides a light converterper se, especially a light converter comprising a matrix containing an inorganic luminescent material and an organic luminescent material as defined by formula (I), with G1, G2, G3, G4, G5, G6, X, Y, A, B, C, D, E, I, J, M, L as defined above (and further below).

In yet a further aspect, the invention also provides such organic luminescent material per se, especially an organic luminescent material as defined by formula (I), with G1, G2, G3, G4, G5, G6, X, Y, A, B, C, D, E, I, J, M, L as defined above (and further below).

Advantageously, such organic luminescent material may have a red luminescence (upon UV and/or blue excitation) with does not extend far in the red and has a cutoff at a relative short wavelength (compared to most of the state of the art red luminescent materials similar to formula I phosphors).

As indicated above, organic phosphors (organic luminescent materials) may suffer from a relatively low photochemical stability. Their stability may strongly depend on the temperature of the material and on the amount of light that it converts. For this reason, organic phosphors may be suitable candidates when used in the remote configuration (see below). A lighting assembly using organic remote phosphor is relatively cheap because of the use of relatively cheap organic luminescent material. Furthermore, organic luminescent materials allow an easy design of a specific organic luminescent material which has a light emission spectrum anywhere in visible spectrum. Such molecules can be synthesized and depending on the molecular structure it emits a specific light. These molecules should not have a emission (tail) in the near infrared in order to obtain a high lumen efficiency, which may apply for the above-described organic luminescent material according to formula I.

Especially, the organic luminescent materials are arranged remote from the LED die (i.e. not in physical contact with the LED). The shortest distance between the light source (exit surface), such as a LED (die), and one or more of the luminescent materials, preferably all luminescent materials, may be larger than 0 mm, especially equal to or larger than 0.1 mm, such as 0.2 or more, and in some embodiments even equal to or larger than 10 mm, such as 10-100 mm.

The above described organic luminescent material is of the perylene type. Perylenes are known in the art and are for instance described in U.S. Pat. No. 4,845,223, US 2003/0111649, WO 2010/116294 (incorporated herein by reference), and WO 2012/113884.

The phrase "at least two selected from G2, G3, G4, and G5 at least comprise X, wherein independently at least one of D, E, I, L and M of at least two of said at least two selected from G2, G3, G4, and G5 comprise a group selected from fluorine and chlorine" indicates amongst others that from the four groups G2, G3, G4, and G5, at least two of these, but in embodiments also three of these, or all of these, comprise a group X as defined herein. Especially, two of these, or in embodiments three or all four of these, are X. From this group of at least two X groups, at least two X groups are each independently at least substituted with one fluroine or chlorine, especially at least substituted with one fluorine. This may thus include embodiments where two of G2-G5 comprise X, or even especially are X, with each of them one or more halogen substitutions, but this may also include embodiments where three or four of G2-G5 comprise X, or even especially are X, with two of the three, or three of the three, or two of the four, or three of the four, or four of the four, respectively, are substituted with one or more halogens. In an embodiment, two of G2-G5 comprise (especially consist of) X. In yet another embodiment, four of G2-G5 comprise (especially consist of) X. Hence, the phrase "at least substituted with one fluorine" and similar phrases may indicate that there is at least one substituent F, though there may (thus) be more. As indicated above, the available X-groups in two or more of G2, G3, G4, and G5, may especially comprise two or more groups selected from fluorine and chlorine, i.e. contain two or more halogen substituents.

The phrase "independently at least one of D, E, I, L and M of at least two of said at least two selected from G2, G3, G4, and G5 comprise a group selected from fluorine and chlorine" also indicates that the X groups available are independently of each other substituted. Hence, one of the X groups may e.g. have a fluorine at the D or M position and one of the X groups may have a fluorine at the E or L position, or a chlorine at one more of the D, E, I, L, M position, etc. Especially, the two groups that at least comprise X, or more especially the two groups that in an embodiment are X, are identical. When the four groups comprise X, or are X, especially there are two sets of identical X, but the sets are mutually different, or there is one set of identical X (all four G2-G5 are identical).

It appears that with the inclusion of a halogen in X the emission wavelength shifts to the blue (less far red). For instance, including two X groups each comprising one fluorine substitution, there may be a blue shift of about 10 nm relative to the unsubstituted X groups. With two X groups each comprising two fluorine substitutions, the shift to the blue may be in the range of 20 nm relative to the unsubstituted X groups. Hence, in a specific embodiment independently at least two of D, E, I, L and M of at least two of said at least two selected from G2, G3, G4, and G5 comprise groups selected from fluorine and chlorine. Hence, assuming 2-4 of G2-G5 comprising, or especially consisting of X, at least two of these (i.e. two of two, two of the three, or three of the three, or two of the four, or three of the four, or four of the four) have two or more halogen groups. The distribution of these two or more halogens over D, E, I, L and M for each of these at least two G2-G5 may independently be chosen. However, as indicated above, when the two groups at least comprise X, or more especially, when two groups are X, these two groups are in an embodiment especially identical. When the four groups comprise X, or are X, especially there are two sets of identical X (especially one or more of G2=G5 and G3=G4 applies), but the sets are mutually different, or there is one set of identical X (all four G2-G5 are identical).

In an embodiment, the following conditions apply: (I) with respect to Y: (Ia) A,C=isopropyl and B,J,Q=hydrogen; or (Ib) A,Q=t-butyl and B,J,C=hydrogen; and (II) with respect to X: (IIa) D,M=isopropyl and E,I,L=hydrogen or (IIb) one or two of D,E,I,L,M=fluorine or chlorine and the remaining hydrogen. This is indicated in below table:

| | Y | | | | | | X | | | | |
|---|---|---|---|---|---|---|---|---|---|---|---|
| | A | B | C | J | Q | | D | E | I | L | M |
| Ia | iso-propyl | H | iso-propyl | H | H | IIa | iso-propyl | H | H | H | iso-propyl |
| Ia | iso-propyl | H | iso-propyl | H | H | IIb | one or two of D, E, I, L, M = fluorine or chlorine and the remaining hydrogen | | | | |
| Ib | t-butyl | H | H | H | t-butyl | IIa | iso-propyl | H | H | H | iso-propyl |
| Ib | t-butyl | H | H | H | t-butyl | IIb | one or two of D, E, I, L, M = fluorine or chlorine and the remaining hydrogen | | | | |

The options IIa and IIb especially independently apply to at least two of G2, G3, G4 and G5. More especially, the conditions IIb especially apply to at least two, especially all four, of G2, G3, G4 and G5 (i.e. at least two of G2, G3, G4 and G5 are X, with the conditions IIb).

Note that such conditions for Y may apply to one or both Y groups. The conditions for X may apply to both X comprising groups selected from G2-G5, but may optionally apply to three or four of these four groups. This also applies for the below indicated embodiments. In a specific embodiment, two of the groups G2, G3, G4 and G5 are hydrogen and the two X comprising groups are identical.

In a further specific embodiment, G2=G5=X, with D=E=F and I=L=M=hydrogen, and wherein G1=G6=Y, with A=C=isopropyl and B=J=Q=hydrogen. This is a specific embodiment of the combination Ia-IIb as indicated in the table. Such embodiment may especially show a desired luminescence.

Likewise, a further desired embodiment is wherein G2=G3=G4=G5 are X, with at least one of A or B is a fluorine or chlorine, and wherein C, J, Q are independently selected from F, Cl, or H.

Alternatively, G2=G5=X, with D=E=F and I=L=M=hydrogen, and wherein G1=G6=Y, with at least one of A or B is a fluorine or chlorine, and wherein C, J, Q are independently selected from F, Cl, or H. In such embodiment, G3 and G4 may especially be hydrogen.

Alternatively, G2=G4=X, with D=E=F and I=L=M=hydrogen, and wherein G1=G6=Y, with at least one of A or B is a fluorine or chlorine, and wherein C, J, Q are independently selected from F, Cl, or H. In such embodiment, G3 and G5 may especially be hydrogen.

Another specific embodiment is wherein G2=G5=X, with D=E=F and I=L=M=hydrogen, and wherein G1=G6=Y, with A=C=isopropyl and B=J=Q=hydrogen. In such embodiment, G3 and G4 may especially be hydrogen.

Alternatively, G2=G4=X, with D=E=F and I=L=M=hydrogen, and wherein G1=G6=Y, with A=C=isopropyl and B=J=Q=hydrogen. In such embodiment, G3 and G5 may especially be hydrogen.

With respect to G1 and G6, it may be advantageous (with respect to optical properties (of especially the light converter)) when either A=C=isopropyl and B=J=Q=hydrogen, or when A=Q=t-butyl and B=J=C=hydrogen.

The red emitting (organic) luminescent material preferably emits 70% of the energy (Watt) below 650 nm (at RT), even more especially at least 70% of the energy below 645 nm (at RT).

The above described organic luminescent material may be well excitable in the blue and/or UV and/or even in the green and/or yellow. Hence, in further embodiments, the organic luminescent material may be excited by a source of blue light, such as a blue LED light source, but alternatively or additionally, the organic luminescent material may also be excited by a source of green and/or yellow light. Examples of the latter may e.g. green and/or yellow emitting luminescent materials like cerium containing garnet systems (such as YAG:Ce; see also below) or an organic yellow emitter.

In a further aspect, the compound herein indicated with reference 17 (see also FIG. 2b) is used in a remote (from the light source) configuration. In yet another embodiment, the compound herein indicated with reference 17 is embedded in a matrix comprising PET. Especially, this PET matrix may be arranged remote (from the light source).

The term "organic luminescent material" may especially refer to an organic material that has luminescent properties (i.e. can emit light upon excitation (by one or more of UV and blue light)). As the organic luminescent material of formula I emits at least in the red, the organic luminescent material is herein also indicated as red emitter or red emitting luminescent material or red luminescent material. However, the organic luminescent material of formula I may also remit in e.g. the yellow.

The term light converter may refer to a system that is configured to convert light from a first wavelength into light of a second wavelength. Especially, UV and/or blue light (excitation wavelength) may be (at least partially) converted into visible light (of higher wavelength than the excitation wavelength).

The light converter may be in the form of for instance particles, flakes, a film, a plate, etc. In a specific embodiment, the term light converter may include a self supporting layer.

Hence, in an embodiment, the light converter is selected from the group consisting of a coating, a self supporting layer, and a plate; which light converter is thus especially solid at room temperature, especially even up to 100° C., especially even up to 150° C., especially even up to 200° C.). The light converter may be flexible or may be rigid. Further, the light converter may be flat or curved (in one or two dimensions). Further, optionally the light converter may comprise outcoupling structures at at least part of the external surface of the light converter.

The light converter may comprise one or more parts, like layers on top of each other. Such parts may comprise different luminescent materials or luminescent materials in different concentration. However, at least part of the light converter comprises the (red) organic luminescent material.

The matrix may especially comprise a matrix material and the above indicated materials such as the organic luminescent material, and optionally inorganic luminescent material, etc. The organic luminescent material(s) and optionally other luminescent materials may in an embodiment especially be evenly distributed throughout the matrix. However, the light converter may also comprise two or more segments, wherein two or more segments have different compositions at least with respect to the luminescent material(s), e.g. with respect to type and/or concentration of the luminescent material(s).

The luminescent material(s) (i.e. at least the organic luminescent material according to formula I, but optionally also including one or more further luminescent materials), may in an embodiment molecularly be distributed through the matrix. Alternatively or additionally, the luminescent material(s) are available as particles, optionally having a coating. In the latter embodiment, coated particles may be embedded in the matrix. The coating may especially be applied to seal such particle from $H_2O$ and/or $O_2$.

Especially, the matrix material is transmissive for light having a wavelength selected from the range of 380-750 nm. For instance, the matrix material may be transmissive for blue, and/or green, and/or red light. Especially, the matrix material is transmissive for at least the entire range of 420-680 nm. Especially, the matrix material may have a light transmission in the range of 50-100%, especially in the range of 70-100%, for light generated by the light source of the lighting unit (see also below) and having a wavelength selected from the visible wavelength range. In this way, the matrix material is transmissive for visible light from the lighting unit. The transmission or light permeability can be determined by providing light at a specific wavelength with a first intensity to the material and relating the intensity of the light at that wavelength measured after transmission through the material, to the first intensity of the light provided at that specific wavelength to the material (see also E-208 and E-406 of the CRC Handbook of Chemistry and Physics, 69th edition, 1088-1989). The light converter may be transparent or translucent, but may especially be transparent. Especially, the light converter is substantially transparent and/or does not substantially scatter light. When the light converter is transparent, light of the light source may not entirely be absorbed by the light converter. Especially when using blue light, this may be of interest, as the blue light may be used to excite the light luminescent materials and may be used to provide a blue component (in white light).

The matrix (material) may comprises one or more materials selected from the group consisting of a transmissive organic material support, such as selected from the group consisting of PE (polyethylene), PP (polypropylene), PEN (polyethylene napthalate), PC (polycarbonate), polymethylacrylate (PMA), polymethylmethacrylate (PMMA) (Plexiglas or Perspex), cellulose acetate butyrate (CAB), silicone, polyvinylchloride (PVC), polyethyleneterephthalate (PET), (PETG) (glycol modified polyethyleneterephthalate), PDMS (polydimethylsiloxane), and COC (cyclo olefin copolymer). However, in another embodiment the matrix (material) may comprise an inorganic material. Preferred inorganic materials are selected from the group consisting of glasses, (fused) quartz, transmissive ceramic materials, and silicones. Also hybrid materials, comprising both inorganic and organic parts may be applied. Especially preferred are PMMA, PET, transparent PC, or glass as material for the matrix (material). Even more especially, the matrix comprises polyethylene terephthalate (PET) as this matrix seems to give the best optical properties compared to other matrices with the same luminescent materials(s). The organic luminescent material degrades (under influence of light source irradiation) slowest in PET.

The light converter may especially be made by combining the luminescent material(s) and optionally other ingredients and one or more precursors of the matrix, followed by a synthesis of the matrix. For instance, in case of polymeric matrix materials this may be done by using monomeric precursors of the polymer and polymerizng the monomric precursors, like by step-growth polymerization, or by radical chain polymerization, etc., in the presence of the luminescent material(s) and optionally other ingredients, to provide the polymeric matrix. Another option may be using as starting material(s) molecules, especially polymers, that are curable, and curing these molecules, especially polymers, in the presence of the luminescent material(s) and optionally other ingredients, to provide the matrix.

In a specific embodiment, one or more of G1, G2, G3, G4, G5, and G6, especially one or more of G1 and G6, comprise a covalent link with the matrix. This may for instance be obtained by providing one or more of these groups, such as one or more of G1 and G6, with a curable group or a polymerizable group. As indicated above, the matrix may e.g. PMMA or PET, especially PET.

The matrix may be coated or enclosed by a seal or coating. The coating or seal may especially be applied to seal such matrix from $H_2O$ and/or $O_2$.

As indicated above, the light converter may especially comprise a green luminescent material and a red luminescent material. The light converter may comprise a plurality of luminescent materials, of which at least one comprises an organic luminescent material according to formula I.

The term "formula (I)" may also be indicated as "chemical formula (I)". However, the light converter may also comprise a plurality of organic luminescent materials according to formula I. Hence, in an embodiment, the term "organic luminescent material" may relate to a combination of different organic luminescent material all complying with formula (I).

Further, the light converter especially comprises an inorganic luminescent material (see further below). However, the light converter may also comprise a plurality of inorganic luminescent materials. Hence, in an embodiment the light converter may comprise one or more organic luminescent materials according to formula I, and optionally one or more other organic luminescent materials, and preferably one or more inorganic luminescent materials. The light converter may further comprise one or more scattering materials, and optionally other materials.

In a specific embodiment, two of the groups G2, G3, G4 and G5 are hydrogen and the two X comprising groups are identical, the inorganic luminescent material comprises a quantum dot based luminescent material, and the matrix comprises polyethylene terephthalate (PET) (see also above).

In a variant, at least two selected from G2, G3, G4, and G5 at least comprise X, wherein independently at least one of D, E, I, L and M of at least two of said at least two selected from G2, G3, G4, and G5 comprise a group as defined above, including optionally, but not necessarily, selected from fluorine and chlorine. Hence, in such variant, one or more of G2, G3, G4, and G5 may be halogen free. For instance, for each of G2, G3, G4, and G5 (at least comprising X) one or more of D, E, I, L and M may comprise independently comprise a group selected from hydrogen, isopropyl, t-butyl, methoxy, alkyl with up to 16 carbon atoms, and an oxygen-containing alkyl with up to 16 carbon atoms.

Herein, it is especially suggested using these "narrow green" emitting phosphor with a narrow emission characteristics with relatively low emission above 600 nm. This may lead to an optimal combination with the above described organic luminescent material according to formula I that is especially emitting in the red.

Hence, one or more further luminescent materials may be applied. The one or more further luminescent materials may also be embedded in the light converter. Alternatively or additionally, the one or more further luminescent materials may be available in a coating on the luminescent light converter. Alternatively or additionally, the one or more further luminescent materials may be arranged within the lighting device separate from the light converter. Especially, the one or more further luminescent materials comprise a narrow green emitting phosphor. This narrow green emitting phosphor may be selected from the group consisting of inorganic luminescent materials. The term "inorganic luminescent material" especially refers to an inorganic material that has luminescent properties (i.e. can emit light upon excitation (by one or more of UV and blue light)). The inorganic luminescent material may especially be configured to emit at least in the green, though other wavelengths are not excluded, like (also) in the red, yellow, green, etc. The term "inorganic luminescent material" especially refers to an inorganic material that has luminescent properties (i.e. can emit light upon excitation (by one or more of UV and blue light)). The inorganic luminescent material may especially be configured to emit at least in the green, though other wavelengths are not excluded, like (also) in the red, yellow, green, etc.

Hence, the inorganic luminescent material as indicated above may especially be configured to provide green light (and optionally other light). Hence, the inorganic luminescent material may especially be configured to convert at least part of the light of the light source into at least green light. The inorganic luminescent material, and especially an inorganic luminescent material (configured to provide green light), may be comprised by the light converter, especially the matrix, but may also be outside the light converter, such as a coating on the light converter.

Especially, the green emitter has a spectral distribution of the emission (at RT) having a bandwidth band ≤100 nm (FWHM; full width half maximum), more preferably a bandwidth band ≤80 nm, most preferably a bandwidth band ≤50 nm (FWHM). This (narrow) band green emitting luminescent material may especially absorb light ≤500 nm. The (narrow) band green emitting luminescent material preferably emits 70% of the energy (Watt) below 600 nm (at RT). Preferably, there is substantially no absorption-emission peak overlap (thereby decreasing self-absorption). The inorganic luminescent material may especially be configured to provide green light (and optionally other light). Hence, the inorganic luminescent material may especially be configured to convert at least part of the light of the light source into at least green light.

Several options for green emitters are possible, including one or more of $(Ca,Sr,Ba)(Al,Ga,In)_2(O,S,Se)_4:Eu^{2+}$, a thiogallate, especially such luminescent material at least comprising Sr, Ga and S, such as $SrGa_2S_4:Eu^{2+}$. These type of luminescent materials may especially be narrow band green emitters.

Optionally or alternatively, the inorganic luminescent material may comprise a $M_3A_5O_{12}:Ce^{3+}$ (garnet material), wherein M is selected from the group consisting of Sc, Y, Tb, Gd, and Lu, wherein A is selected from the group consisting of Al and Ga. Preferably, M at least comprises one or more of Y and Lu, and wherein A at least comprises Al. These types of materials may give highest efficiencies. Embodiments of garnets especially include $M_3A_5O_{12}$ garnets, wherein M comprises at least yttrium or lutetium and wherein A comprises at least aluminum. Such garnet may be doped with cerium (Ce), with praseodymium (Pr) or a combination of cerium and praseodymium; especially however with at least Ce. Especially, A comprises aluminum (Al), however, A may also partly comprise gallium (Ga) and/or scandium (Sc) and/or indium (In), especially up to about 20% of Al, more especially up to about 10% of Al (i.e. the A ions essentially consist of 90 or more mole % of Al and 10 or less mole % of one or more of Ga, Sc and In); A may especially comprise up to about 10% gallium. In another variant, A and O may at least partly be replaced by Si and N. The element M may especially be selected from the group consisting of yttrium (Y), gadolinium (Gd), terbium (Tb) and lutetium (Lu). Further, Gd and/or Tb are especially only present up to an amount of about 20% of M. In a specific embodiment, the garnet luminescent material comprises $(Y_{1-x}Lu_x)_3Al_5O_{12}:Ce$, wherein x is equal to or larger than 0 and equal to or smaller than 1. The term ":Ce" or ":$Ce^{3+}$", indicates that part of the metal ions (i.e. in the garnets: part of the "M" ions) in the luminescent material is replaced by Ce. Especially a lutetium comprising garnet may provide the desired luminescence, especially when lutetium is at least 50% of M.

Additionally or alternatively, the inorganic luminescent material may comprise quantum Dots (QDs). Amongst other narrow band emitters quantum dots are highly suitable for this purpose. Quantum dots are small crystals of semiconducting material generally having a width or diameter of only a few nanometers. When excited by incident light, a quantum dot emits light of a color determined by the size and material of the crystal. Light of a particular color can therefore be produced by adapting the size of the dots. This means that by using quantum dots any spectrum can be obtained as they are narrow band emitters.

Most known quantum dots with emission in the visible range are based on cadmium selenide (CdSe) with shell such as cadmium sulfide (CdS) and zinc sulfide (ZnS). Cadmium free quantum dots such as indium phosphide (InP), and copper indium sulfide (CuInS2) and/or silver indium sulfide ($AgInS_2$) can also be used. Quantum dots show very narrow emission band and thus they show saturated colors. Furthermore, the emission color can easily be tuned by adapting the size of the quantum dots.

The quantum dots or luminescent nanoparticles, which are herein indicated as light converter nanoparticles, may for instance comprise group II-VI compound semiconductor quantum dots selected from the group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe and HgZnSTe. In another embodiment, the luminescent nanoparticles may for instance be group III-V compound semiconductor quantum dots selected from the group consisting of GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs. In yet a further embodiment, the luminescent nanoparticles may for instance be I-III-VI2 chalcopyrite-type semiconductor quantum dots selected from the group consisting of $CuInS_2$, $CuInSe_2$, $CuGaS_2$, $CuGaSe_2$, $AgInS_2$, $AgInSe_2$, $AgGaS_2$, and $AgGaSe_2$. In yet a further embodiment, the luminescent nanoparticles may for instance be I-V-VI2 semiconductor quantum dots, such as selected from the group consisting of $LiAsSe_2$, $NaAsSe_2$ and $KAsSe_2$. In yet a further embodiment, the luminescent nanoparticles may for instance be a group IV-VI compound semiconductor nano crystals such as SbTe. In a specific embodiment, the luminescent nanoparticles are selected from the group consisting of InP, $CuInS_2$, $CuInSe_2$, CdTe, CdSe, CdSeTe, $AgInS_2$ and $AgInSe_2$. In yet a further embodiment, the luminescent nanoparticles may for instance be one of the group II-VI, III-V, I-III-V and IV-VI compound semiconductor nano crystals selected from the materials described above with inside dopants such as ZnSe:Mn, ZnS:Mn. The dopant elements could be selected from Mn, Ag, Zn, Eu, S, P, Cu, Ce, Tb, Au, Pb, Tb, Sb, Sn and Tl. Herein, the luminescent nanoparticles based luminescent material may also comprise different types of QDs, such as CdSe and ZnSe:Mn.

It appears to be especially advantageous to use II-VI quantum dots. Hence, in an embodiment the semiconductor based luminescent quantum dots comprise II-VI quantum dots, especially selected from the group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe and HgZnSTe, even more especially selected from the group consisting of CdS, CdSe, CdSe/CdS and CdSe/CdS/ZnS.

In an embodiment, Cd-free QDs are applied. In a specific embodiment, the light converter nano-particles comprise III-V QDs, more specifically an InP based quantum dots, such as a core-shell InP—ZnS QDs. Note that the terms "InP quantum dot" or "InP based quantum dot" and similar terms may relate to "bare" InP QDs, but also to core-shell InP QDs, with a shell on the InP core, such as a core-shell InP–ZnS QDs, like a InP—ZnS QDs dot-in-rod.

Typical dots are made of binary alloys such as cadmium selenide, cadmium sulfide, indium arsenide, and indium phosphide. However, dots may also be made from ternary alloys such as cadmium selenide sulfide. These quantum dots can contain as few as 100 to 100,000 atoms within the quantum dot volume, with a diameter of 10 to 50 atoms. This corresponds to about 2 to 10 nanometers. For instance, spherical particles such as CdSe, InP, or $CuInSe_2$, with a diameter of about 3 nm may be provided. The luminescent nanoparticles (without coating) may have the shape of spherical, cube, rods, wires, disk, multi-pods, etc., with the size in one dimension of less than 10 nm. For instance, nanorods of CdSe with the length of 20 nm and a diameter of 4 nm may be provided. Hence, in an embodiment the semiconductor based luminescent quantum dots comprise core-shell quantum dots. In yet another embodiment, the semiconductor based luminescent quantum dots comprise dots-in-rods nanoparticles. A combination of different types of particles may also be applied. For instance, core-shell particles and dots-in-rods may be applied and/or combinations of two or more of the afore-mentioned nano particles may be applied, such as CdS and CdSe. Here, the term "different types" may relate to different geometries as well as to different types of semiconductor luminescent material. Hence, a combination of two or more of (the above indicated) quantum dots or luminescent nano-particles may also be applied.

One example, such as derived from WO 2011/031871, of a method of manufacturing a semiconductor nanocrystal is a colloidal growth process.

In an embodiment, nanoparticles can comprise semiconductor nanocrystals including a core comprising a first semiconductor material and a shell comprising a second semiconductor material, wherein the shell is disposed over at least a portion of a surface of the core. A semiconductor nanocrystal including a core and shell is also referred to as a "core/shell" semiconductor nanocrystal.

For example, the semiconductor nanocrystal can include a core having the formula MX, where M can be cadmium, zinc, magnesium, mercury, aluminum, gallium, indium, thallium, or mixtures thereof, and X can be oxygen, sulfur, selenium, tellurium, nitrogen, phosphorus, arsenic, antimony, or mixtures thereof. Examples of materials suitable for use as semiconductor nanocrystal cores include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing, including ternary and quaternary mixtures or alloys.

The shell can be a semiconductor material having a composition that is the same as or different from the composition of the core. The shell comprises an overcoat of a semiconductor material on a surface of the core semiconductor nanocrystal can include a Group IV element, a Group II-VI compound, a Group II-V compound, a Group III-VI compound, a Group III-V compound, a Group IV-VI compound, a Group I-III-VI compound, a Group II-IV-VI compound, a Group II-IV-V compound, alloys including any of the foregoing, and/or mixtures including any of the foregoing, including ternary and quaternary mixtures or alloys. Examples include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing. For example, ZnS, ZnSe or CdS overcoatings can be grown on CdSe or CdTe semiconductor nanocrystals.

Examples of semiconductor nanocrystal (core)shell materials include, without limitation: red (e.g., (CdSe)ZnS (core) shell), green (e.g., (CdZnSe)CdZnS (core)shell, etc.), and blue (e.g., (CdS)CdZnS (core)shell (see further also above for examples of specific light converter nanoparticles, based on semiconductors.

Therefore, in a specific embodiment, the light converter nanoparticles are selected from the group consisting of core-shell nano particles, with the cores and shells comprising one or more of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe, HgZnSTe, GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs.

In general, the cores and shells comprise the same class of material, but essentially consist of different materials, like a ZnS shell surrounding a CdSe core, etc.

Additionally or alternatively, the inorganic luminescent material may also comprise other luminescent materials, such as one or more of selected from the group consisting of divalent europium containing nitride luminescent material or a divalent europium containing oxonitride luminescent material, such as one or more materials selected from the group consisting of (Ba,Sr,Ca)S:Eu, (Mg,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation, especially in the range of about 0.5-10%, more especially in the range of about 0.5-5% relative to the cation(s) it replaces. The term ":Eu" or ":Eu$^{2+}$", indicates that part of the metal ions is replaced by Eu (in these examples by Eu$^{2+}$). For instance, assuming 2% Eu in CaAlSiN$_3$:Eu, the correct formula could be (Ca$_{0.98}$Eu$_{0.02}$)AlSiN$_3$. Divalent europium will in general replace divalent cations, such as the above divalent alkaline earth cations, especially Ca, Sr or Ba. The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50-100%, especially 50-90% Ba and 50-0%, especially 50-10% Sr, such as Ba$_{1.5}$Sr$_{0.5}$.Si$_5$N$_8$:Eu, (i.e. 75% Ba; 25% Sr). Here, Eu is introduced and replaces at least part of M i.e. one or more of Ba, Sr, and Ca). Likewise, the material (Ba,Sr,Ca)AlSiN$_3$:Eu can also be indicated as MAlSiN$_3$:Eu wherein M is one or more elements selected from the group consisting of barium (Ba)$_5$ strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Preferably, in an embodiment the inorganic luminescent material comprises (Ca,Sr, Mg)AlSiN$_3$:Eu, preferably CaAlSiN$_3$:Eu. Further, in another embodiment, which may be combined with the former, the inorganic luminescent material comprises (Ca, Sr,Ba)$_2$Si$_5$N$_8$:Eu, preferably (Sr,Ba)$_2$Si$_5$N$_8$:Eu. The terms "(Ca,Sr,Ba)" indicate that the corresponding cation may be occupied by calcium, strontium or barium. It also indicates that in such material corresponding cation sites may be occupied with cations selected from the group consisting of calcium, strontium and barium. Thus, the material may for instance comprise calcium and strontium, or only strontium, etc.

The inorganic luminescent material may also comprise one or more luminescent materials selected from the group consisting of a trivalent cerium containing garnet (see above) and a trivalent cerium containing oxonitride. The oxonitride materials are in the art often also indicated as oxynitride materials.

Hence, in an embodiment the inorganic luminescent material is configured to provide at least green light, the organic luminescent material is configured to provide at least red light, and especially the light source is configured to provide blue light. As indicated the inorganic luminescent material comprises a quantum dot based luminescent material.

The term "inorganic luminescent material" may thus also relate to a plurality of different inorganic luminescent materials. The inorganic luminescent material may be comprised by the light converter, such as embedded in the matrix, like especially the organic luminescent material, or may be outside the light converter, such as a layer on the light converter, or may be elsewhere in the lighting device. Combinations of two or more of such configurations are also possible. Hence, in an embodiment the inorganic luminescent material, such as the quantum dot based luminescent material, is embedded in the matrix.

As indicated above, the lighting device comprises (a) a light source configured to generate light source light, and (b) a light converter configured to convert at least part of the light source light into visible converter light.

The light converter, or especially the luminescent material, is configured to convert at least part of the light source light. In order words, one may say that the light source is radiationally coupled to the light converter, especially the luminescent material. When the light source comprises a substantially UV light emitting light source, the luminescent material may be configured to convert substantially all light source light that impinges on the luminescent material. In case the light source is configure to generate blue light, the luminescent material may partly convert the light source light. Dependent upon the configuration, a part of the remaining light source light may be transmitted through a layer comprising the luminescent material. Here, the term may relate to one or more of the organic luminescent material and the inorganic luminescent material.

The term light source may in principle relate to any light source known in the art, but may especially refers to a LED-based light source, herein further indicated as LED. The description below will—for the sake of understanding—only addresses LED-based light sources. The light source is configured to provide UV and/or blue light. In a preferred embodiment, the light emitting diode is configured to generate LED light with a blue component. In other words, the light source comprises a blue LED. Hence, in an embodiment, the light source is configured to generate blue light. Especially, the LED is a solid state LED.

In yet another embodiment, the light emitting diode is configured to generate LED light with a UV component. In other words, the light source comprises a UV LED. When a UV light source is applied and blue or white light is desired, as blue component, for instance the well-known materials $BaMgAl_{10}O_{17}:Eu^{2+}$ and/or $(Sr,Ba,Ca)_5(PO_4)_3Cl:Eu^{2+}$ may be applied. However, also other luminescent materials that are able to convert UV light into blue light may alternatively or additionally be applied. Such blue luminescent material may be applied as part of the light source, or remote, and may optionally (also) be comprised by the light converter. All luminescent materials described herein may be radiationally coupled with the light source, though optionally one or more luminescent materials are radiationally coupled with one or more other luminescent materials (i.e. they are configured to receive mission light of those one or more other luminescent materials, and can get be excited by that emission light).

Preferably, the light source is a light source that during operation emits at least light at a wavelength selected from the range of 200-490 nm, especially a light source that during operation emits at least light at wavelength selected from the range of 400-490 nm, even more especially in the range of 440-490 nm. This light may partially be used by the luminescent material(s) (see below). In a specific embodiment, the light source comprises a solid state LED light source (such as a LED or laser diode). The term "light source" may also relate to a plurality of light sources, such as 2-20 (solid state) LED light sources. Hence, the term LED may also refer to a plurality of LEDs. Hence, in a specific embodiment, the light source is configured to generate blue light. In a further embodiment, the lighting device might be applied as back lighting unit in an LCD application. Hence, the invention provides in a further aspect a liquid crystal display device comprising a back lighting unit, wherein the back lighting unit comprises one or more lighting devices as defined herein.

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL.

In an embodiment, the light source may also provide light source light having a correlated color temperature (CCT) between about 5000 and 20000 K, e.g. direct phosphor converted LEDs (blue light emitting diode with thin layer of phosphor for e.g. obtaining of 10000 K). Hence, in a specific embodiment the light source is configured to provide light source light with a correlated color temperature in the range of 5000-20000 K, even more especially in the range of 6000-20000 K, such as 8000-20000 K. An advantage of the relative high color temperature may be that there may be a relative high blue component in the light source light.

The lighting device comprises at least the light converter comprising the organic luminescent material according to formula I. Other luminescent materials, may also be present. The one or more other luminescent materials may each individually be comprised by the matrix but may also be provides as coating or layer on the matrix, or may be arranged elsewhere in the lighting device.

The lighting device may especially be configured to be able to provide white light. Optionally, the lighting device is configured to provide colored light or is configured to be able to provide color light and white light, depending upon how the lighting device is controlled.

The terms "violet light" or "violet emission" especially relates to light having a wavelength in the range of about 380-440 nm. The terms "blue light" or "blue emission" especially relates to light having a wavelength in the range of about 440-490 nm (including some violet and cyan hues). The terms "green light" or "green emission" especially relate to light having a wavelength in the range of about 490-560 nm. The terms "yellow light" or "yellow emission" especially relate to light having a wavelength in the range of about 540-570 nm. The terms "orange light" or "orange emission" especially relate to light having a wavelength in the range of about 570-600. The terms "red light" or "red emission" especially relate to light having a wavelength in the range of about 600-750 nm. The term "pink light" or "pink emission" refers to light having a blue and a red component. The terms "visible", "visible light" or "visible emission" refer to light having a wavelength in the range of about 380-750 nm.

The light source may be configured in a chamber, with reflective wall(s) (such as coated with a reflective material like $TiO_2$), and a light transmissive window. In an embodiment, the window is the light conversion layer. In yet a further embodiment, the window comprises the light conversion layer. This layer may be arranged upstream of the window or downstream of the window. In yet a further embodiment, light conversion layers are applied at both sides of the window.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

It may be advantageous, in view of efficiency and/or stability, to arrange the light converter (and optionally also other luminescent material(s) not within the light converter), at a non-zero distance, such as 0.5-50 mm, like 1-50 mm, from the light source. Hence, in an embodiment, the light converter may be configured at a non-zero distance of the light source. For instance, the light converter, or especially the (organic) luminescent material(s), may be applied to or may be comprised by a window of the lighting unit. Hence, in an embodiment, the light converter is configured at a non-zero distance from the light source. Note however that the invention is not limited to applications wherein the distance between the light converter and the light source is non-zero. The invention, and the herein described specific embodiments, may be also applied in other embodiments wherein the light source and light converter are in physical contact. In such instances, the light converter may especially be configured in physical contact with e.g. a LED die.

In case the light source is configured to provide blue light, the luminescent material may be configured to convert only part of the light source light. In an embodiment, the blue light of the light source and the light of the organic luminescent material light and the light of the optional inorganic luminescent material, such as a nano particles based luminescent material, together may in an embodiment provide white light.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
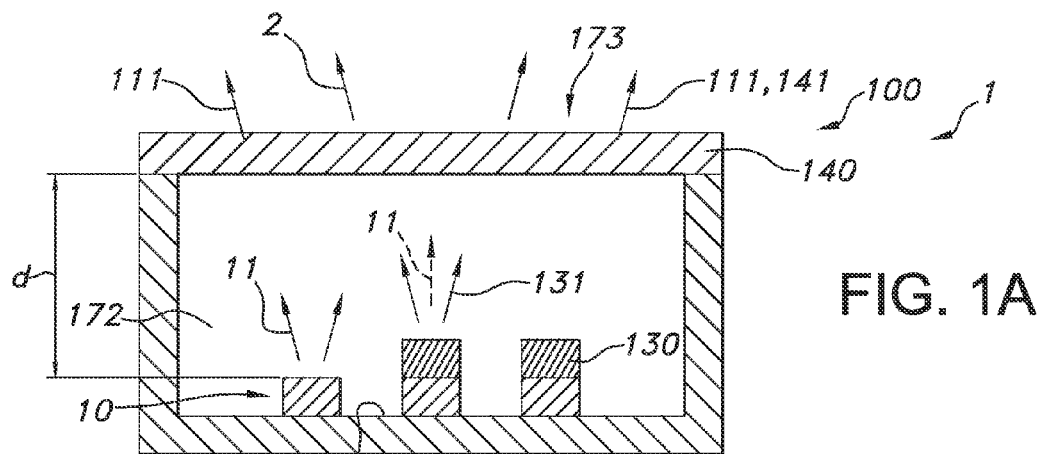
FIGS. 1a-1f schematically depict some embodiments of the lighting device; these drawings are not necessarily on scale.

FIG. 1a schematically depicts a lighting device 1 with a light converter 100, which in this embodiment at least comprises the organic luminescent material 140 according to formula 1. The organic luminescent material 140 is in this embodiment embedded in a (polymeric) matrix, such as PET. As can be seen, a remote version is shown, with a non-zero distance d between the luminescent material (in the light converter 100) and the light source(s), indicated with reference(s) 10. The lighting device 1 comprises one or more light sources 10 which are configured to provide light source light 11, especially blue and/or UV light. The lighting device 1 may comprise a plurality of such light sources. When lighting device light, indicated with reference 2, of a white nature is desired, it may be necessary to us an RGB concept, wherein the red color, or at least part thereof, is provided by the red luminescent material 140, and the blue and green light are provided by one or more of the light source and a combination of the light source and another luminescent material, especially the inorganic luminescent material. The inorganic luminescent material is indicated with reference 130, and provides inorganic luminescent material light 131.

The organic luminescent material 140 according to formula I provides upon excitation by the light source light 11 and/or by emission of one or more other luminescent materials, such as e.g. the inorganic luminescent material light 131, organic luminescent material light 141. Here, the light converter 100 is remote from the light source 10, and the organic luminescent material, which is embedded in the light converter 100, is thus also remote. The optional inorganic luminescent material 130 can also be arranged remote, see below, but is by way of example close to the light source 10, such as in a dome and/or as layer on the LED die.

Just by way of example, one light source has been depicted without the inorganic luminescent material 130. However, in another embodiment, all light sources 10 may be configured with at least inorganic luminescent material 130. Also, by way of example three light sources 10 have been depicted. However, more or less than three light sources may be applied.

Note that the light source 10 may provide blue and/or UV light. The inorganic luminescent material 130 may especially, upon excitation (by said light of the light source 10) provide one or more of blue, green, and yellow light. Optionally, the inorganic luminescent material 130 may also provide red light, but especially the inorganic luminescent material 130 has a cutoff equal to or below 600 nm (such as especially having a spectral distribution with at least 70% of the energy below 600 nm).

FIG. 1a, and other figures, schematically depict a device with a light chamber 170, with an enclosure 171, at least partly enclosing a cavity 172, which has a transmissive part 173. In an embodiment, the transmissive part 173 comprises the light converter 100, or may especially consist of the light converter 100. The surface of the non-transmissive part of the enclosure is indicated with reference 171. At least part of the surface 171 may comprise a reflector, such as a reflective coating.

The light converter 100 provides upon excitation light converter light 111, which at least comprises organic luminescent material light 141 but may optionally comprise other luminescence light as well (see below). The lighting device light, indicated with reference 2, at least comprises light converter light 111/organic luminescent material light 141, but may optionally comprise one or more of the light source light 11, inorganic luminescent material light 131, and light of other luminescent materials (not depicted).

Figure 1B:
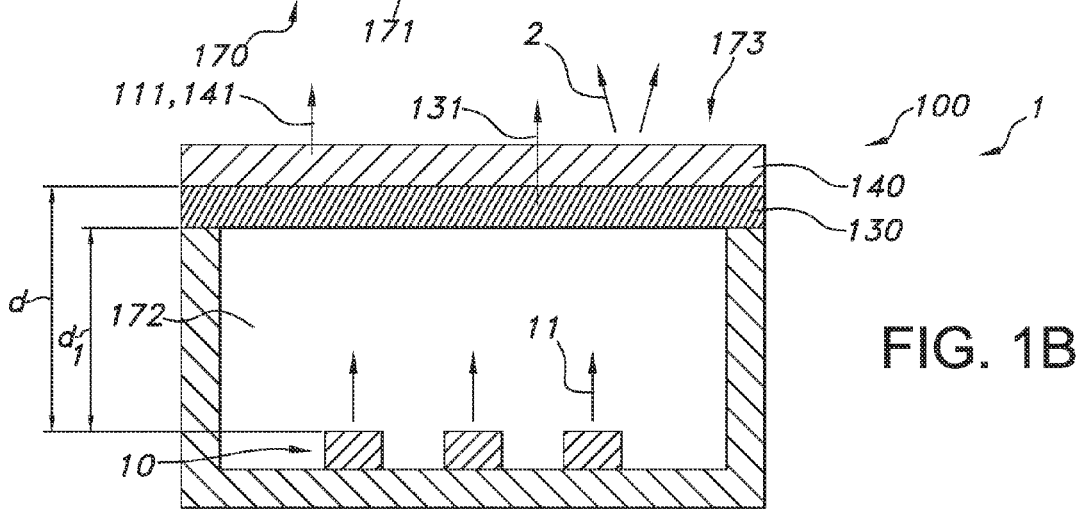

FIG. 1b schematically depicts an embodiment wherein the light converter 100 may comprise an upstream layer with inorganic luminescent material 130. Optionally, this may be a light converter comprising two layers comprising the same matrix, but comprising different luminescent materials. The distance of the layer with inorganic luminescent material 130 to the light source is indicated with d1. This distance is in this embodiment non-zero, in contrast to the embodiment schematically depicted in FIG. 1a.

Figure 1C:
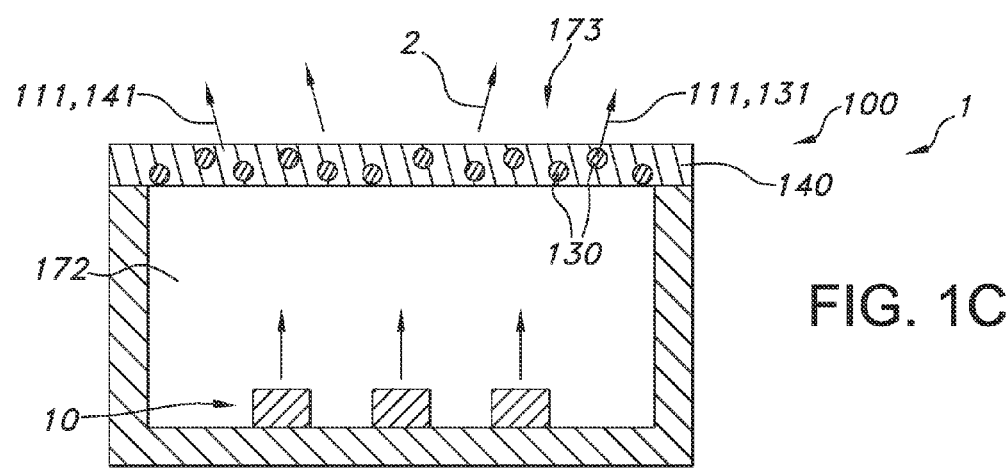

FIG. 1c schematically depicts an embodiment wherein the light converter 100 comprises the inorganic luminescent material 140, e.g. in the form of quantum dots, and the organic luminescent material 130 according to formula I. Both the organic luminescent material 140 and the inorganic luminescent material 130 are in this embodiment embedded in the (remote) light converter, i.e. embedded in the (polymeric) matrix of the light converter 100.

Figure 1D:
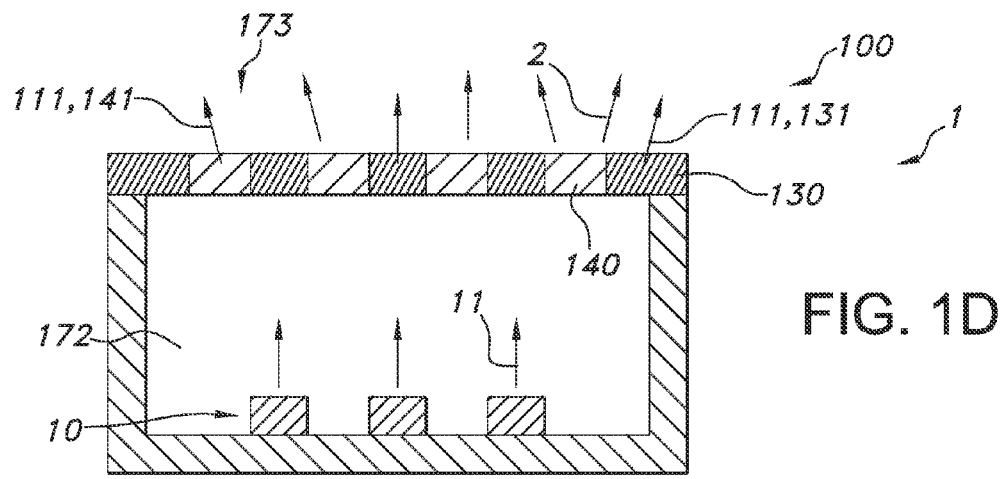

FIG. 1d schematically depicts an embodiment wherein the transmissive part 173 comprises at least two types of segments, with volumes over 0.25 cm$^3$, wherein the two types of segments comprise different weight ratios organic luminescent material and inorganic luminescent material. For instance, first segments only comprise the organic luminescent material 140 as luminescent material and second segments only comprises inorganic luminescent material 130 as luminescent material. The organic luminescent material 140 may also in this embodiment be embedded in a (polymeric) matrix, such as PET. Likewise, also the inorganic luminescent material 130 may be embedded in a (polymeric) matrix, such as PET.

Figure 1E:
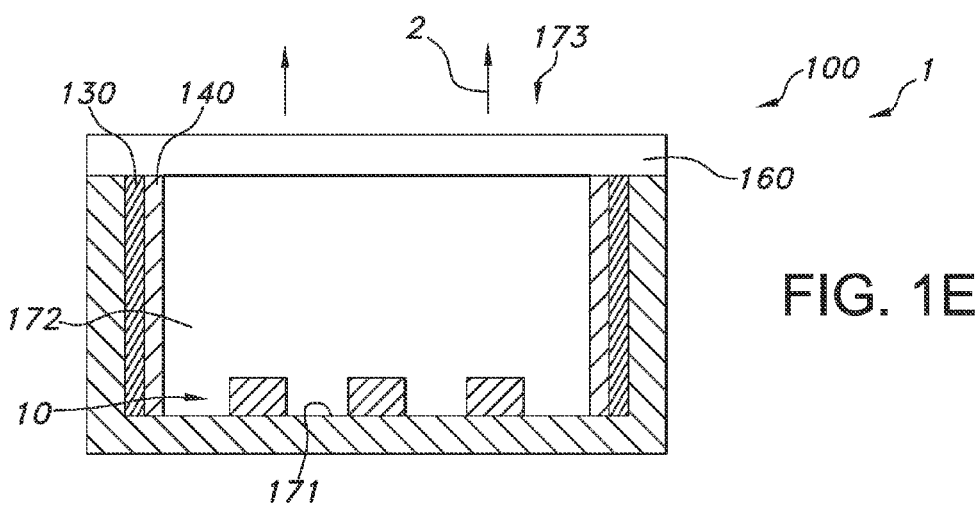

FIG. 1e schematically depicts an embodiment wherein the enclosure 170 comprises a transmissive diffuser 160 (as transmissive part 173) and the light converter is applied to at least part of the non-transmissive part of the enclosure 171.

Figure 1F:
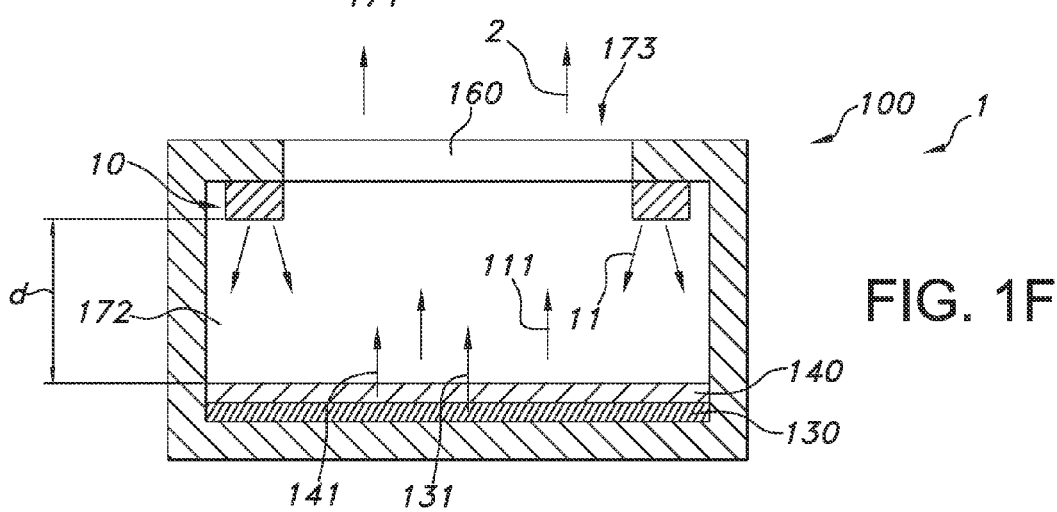

FIG. 1f schematically depicts a reflective configuration. As mentioned above, the organic luminescent material 140 and optionally the inorganic luminescent material 140 may (both) be embedded in a (polymeric) matrix.

Figure 2A:
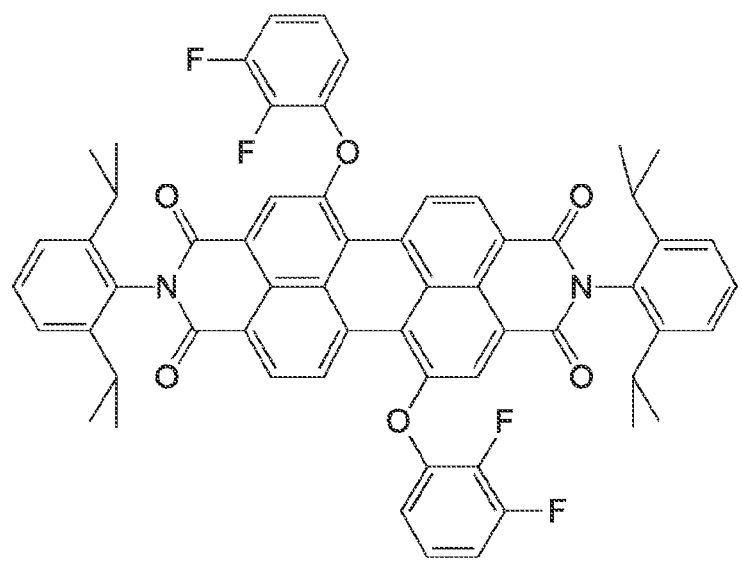
FIGS. 2a-2j schematically depict some organic materials that were made.
Figure 2B:
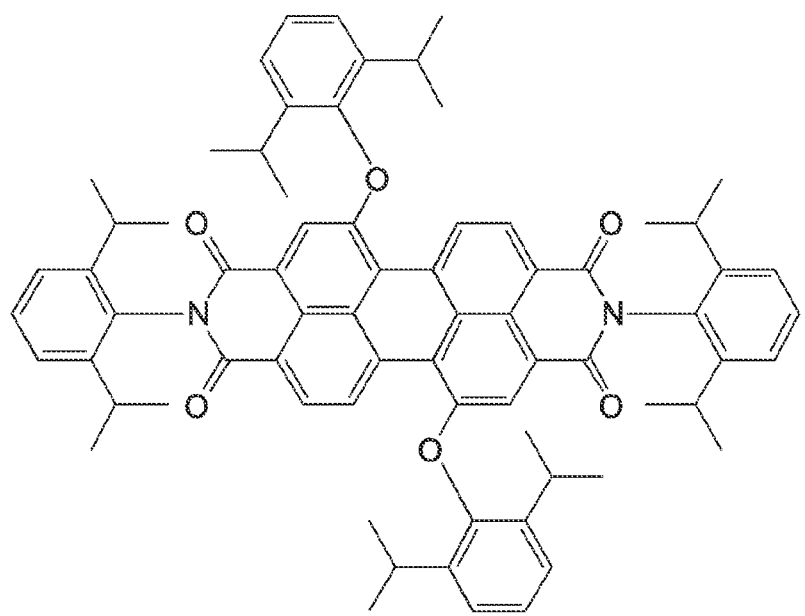
Figure 2C:
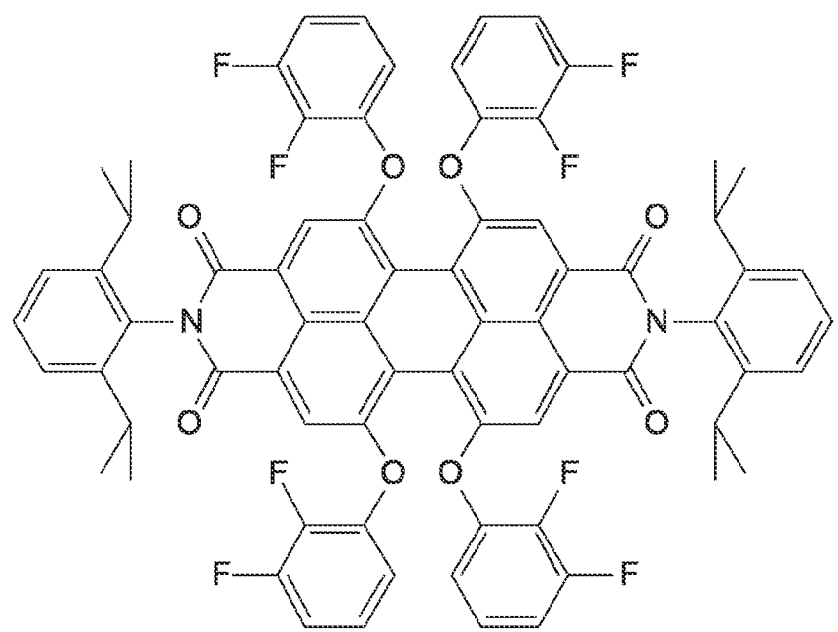

FIGS. 2a-2j schematically depict some organic luminescent material that have been made of the perylene type, especially embodiments of the organic luminescent material 140. Especially molecules 68, 65, 53, 52, 63, 64, x1, and x2 are desired because of their optical properties, especially those having at least two halogen atoms at each X group. Optical properties of some of the luminescent materials are shown in FIGS. 3a and 3b. These graphs show emission spectra, with amongst others emission curve of material 2 as comparison. When measuring the spectral distribution of the emission energy (power) as a function of the emission wavelength under 450 nm excitation in the range up to 750 nm, then the ratio of e.g. below 645 nm emission to the total emission can be calculated.

Figure 4A:
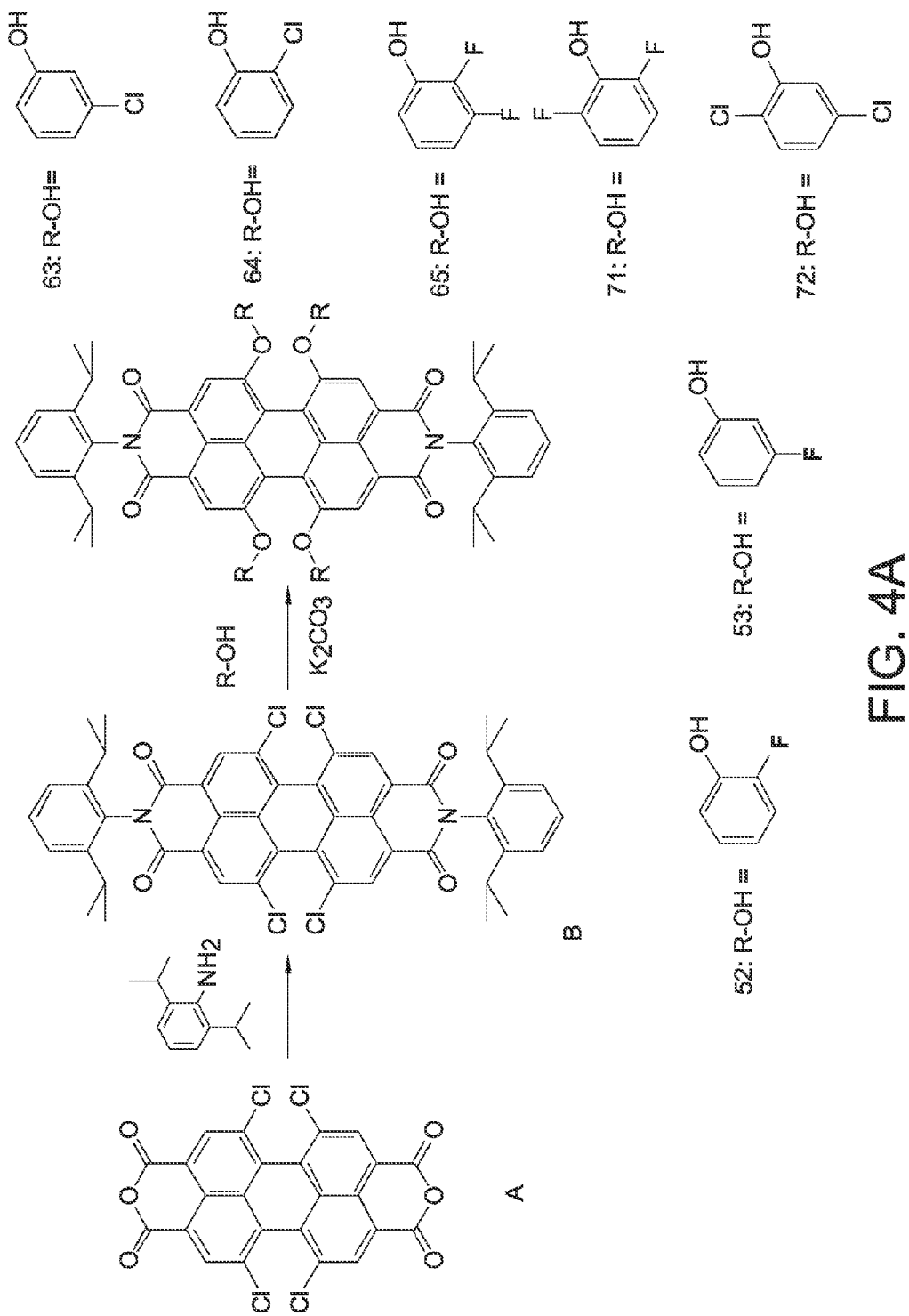
FIGS. 4a-4b schematically show some synthesis schemes.
Figure 4B:
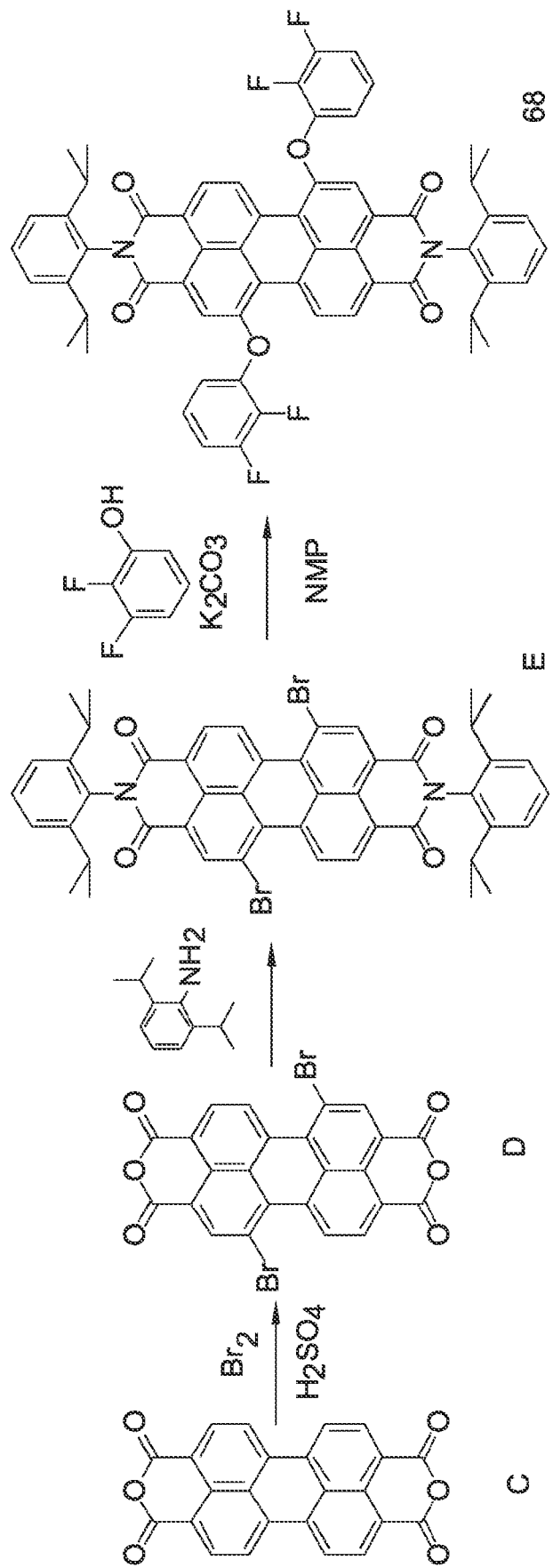

Most of the materials were made according to scheme 1 depicted in FIG. 4a or according to scheme 2 depicted in FIG. 4b.

EXAMPLES

Synthesis of 53. See scheme 1,N,N'-Bis-(2,6-diisopropylphenyl)-1,6,7,12-tetrachloroperylene-3,4,9,10-tetracarboxdiimide B 1,6,7,12-Tetrachloroperylene-3,4:9,10-tetracarboxylic dianhydride; (A, 10.0 g, 19.0 mmol) was finely suspended in propionic acid (250 mL). Then, 2,6-diisopropylaniline (16.7 g, 40 mmol) was added and the mixture was refluxed under nitrogen for 17 h. After cooling to room temperature, water was added to the mixture and the precipitate was filtered, washed extensively with water and then with heptane and dried under vacuum to give 9 g (56% yield) of compound B as an orange solid.

N,N'-Bis(2,6-diisopropylphenyl)-1,6,7,12-tetra(3-fluorophenoxy)perylene-3,4:9,10-tetracarboxdiimide 53

A mixture of N,N'-Bis-(2,6-diisopropylphenyl)-1,6,7,12-tetrachloroperylene-3,4,9,10-tetracarboxdiimide (B, 4 g, 4.7 mmol), 2-fluorophenol (2.5 mL, 28.2 mmol) and K$_2$CO$_3$ (4.3 g, 31.0 mmol) in NMP (80 mL) was stirred at 110° C. under nitrogen for 3 h. Then, the contents of the flask were poured into a mixture of water and acetic acid and stirred for 2 h and the precipitated solid was filtered, washed neutral with warm water and vacuum dried at 60° C. The compound was recrystallized from methanol then from a EtOAc/heptanes mixture (2×) then from a DCM/heptanes mixture (3×) and the red solid collected was washed with warm heptane and dried under vacuum. Pure compound 53 (1.6 g, 19% yield) was obtained as a red solid. $^{19}$F-NMR (282 MHz, in CDCl$_3$): δ=−110 ppm. Mass (TOF-ESI, m/z): Calculated for C$_{72}$H$_{55}$F$_4$N$_2$O$_8{}^+$ ([M-H]$^+$): 1151.39. Found: 1151.61. $\lambda_{max}$ (ethyl acetate)=558 nm, ε=45600. λ (em) (ethyl acetate) 586 nm.

Figure 2D:
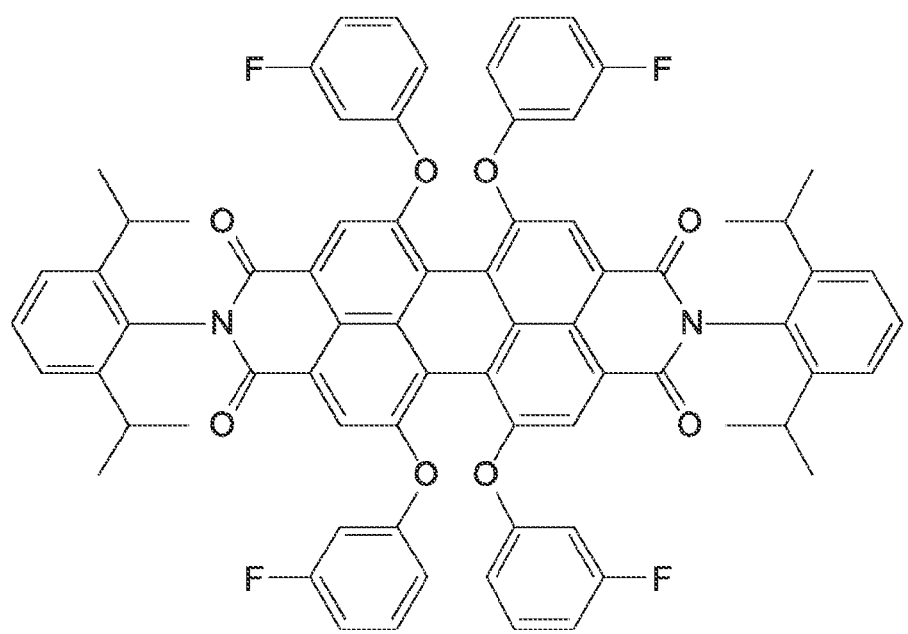
Figure 2E:
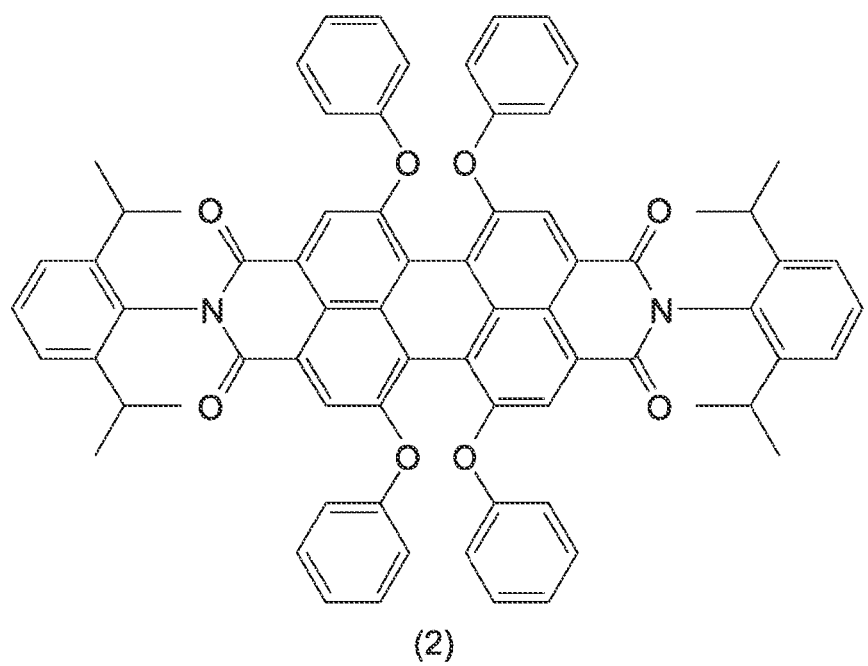
Figure 2F:
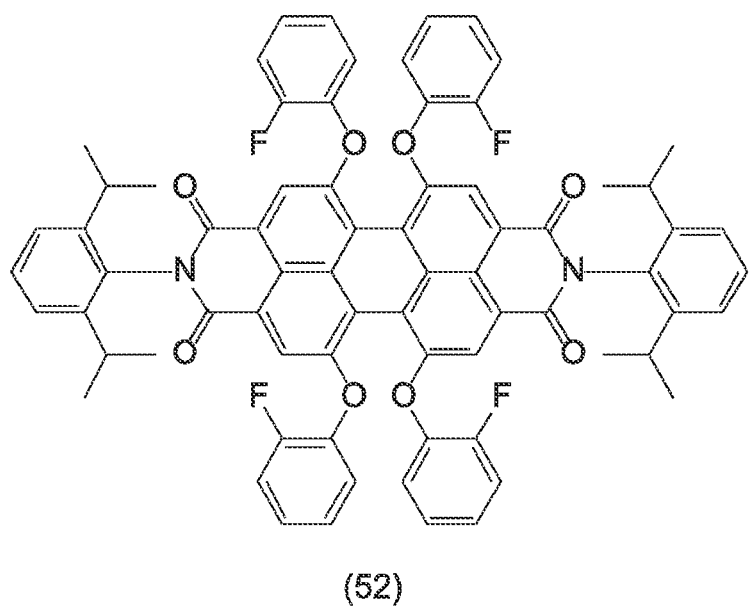
Figure 2G:
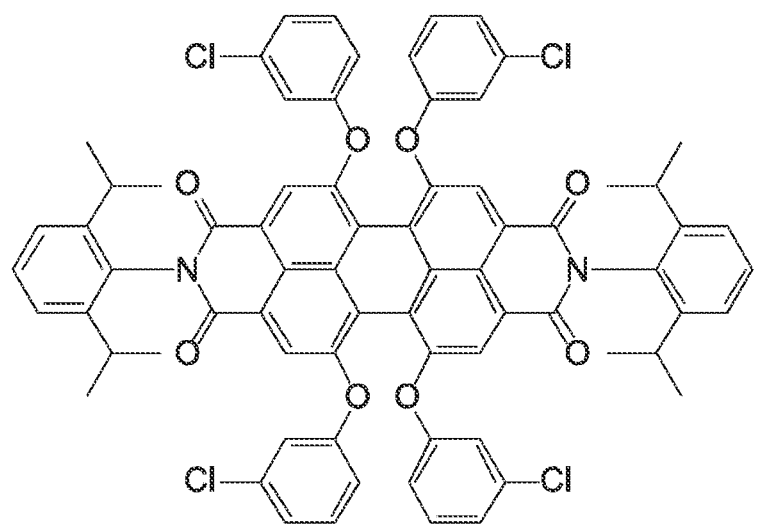
Figure 2H:
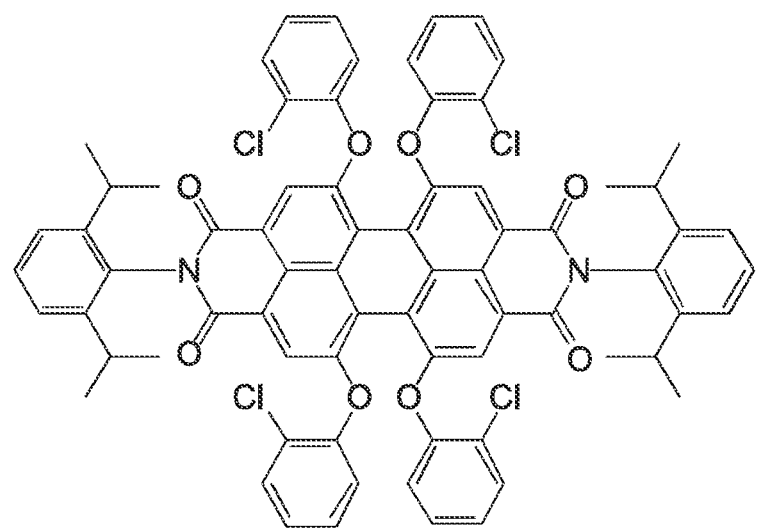
Figure 2I:
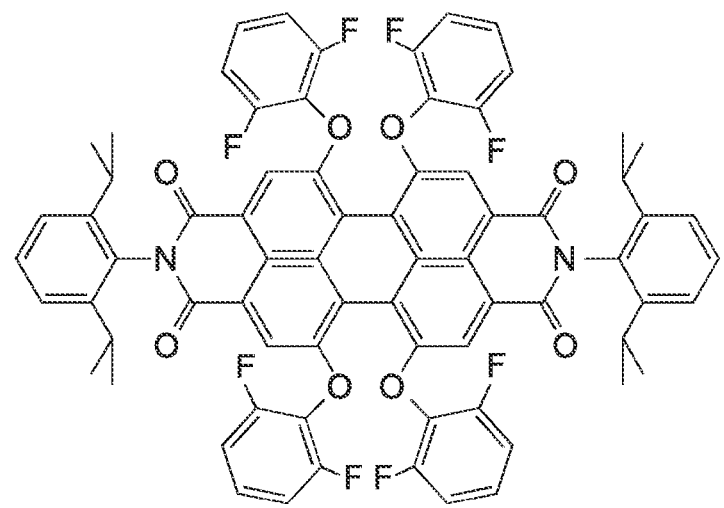
Figure 2J:
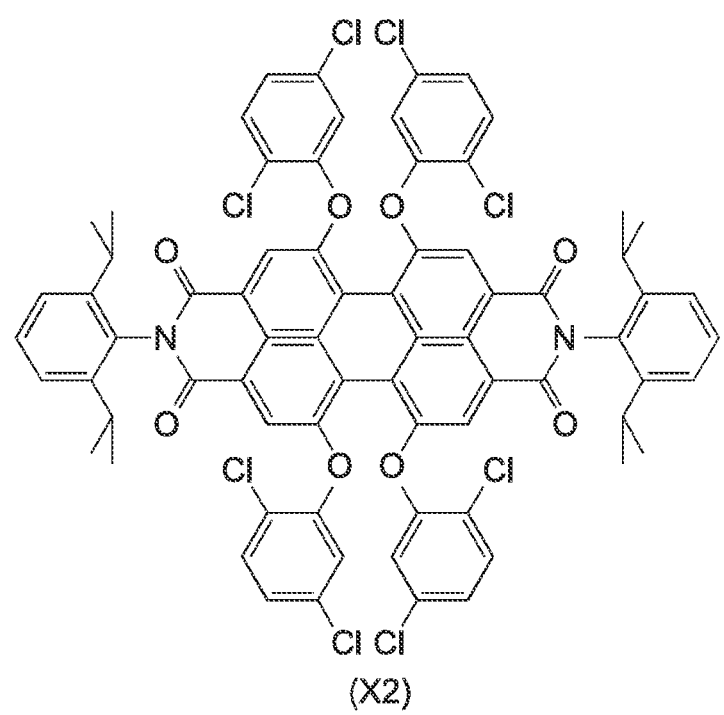
Figure 3A:
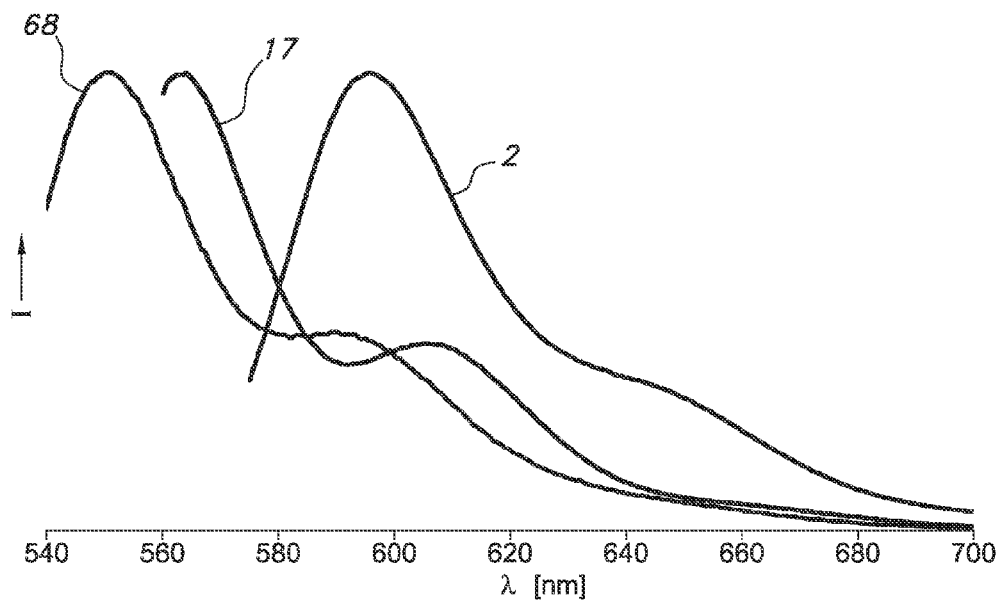
FIGS. 3a-3b show some emission spectra of some of these organic materials.
Figure 3B:
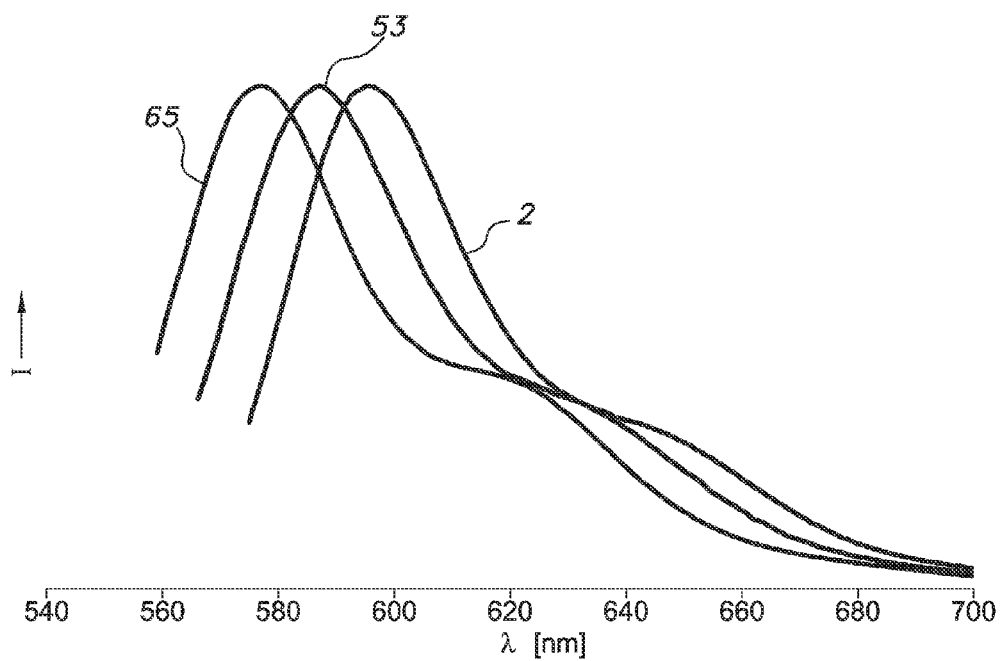

Molecule 53 is depicted in FIG. 2D. As can be seen form this figure, at least two selected from G2, G3, G4, and G5 at least comprise X, wherein independently at least one of D, E, I, L and M of at least two of said at least two selected from G2, G3, G4, and G5 comprise a group selected from fluorine and chlorine. Here, G2, G3, G4 and G5 comprise X, with each of these four comprise a (single) fluorine. Note that not necessarily all four of G2, G3, G4 and G5 comprise identical groups.

Synthesis of N,N'-Bis(2,6-diisopropylphenyl)-1,6,7,12-tetra(2,3-difluorophenoxy) perylene-3,4,9,10-tetracarboxdiimide 65. See scheme 1

A mixture of N,N'-Bis-(2,6-diisopropylphenyl)-1,6,7,12-tetrachloroperylene-3,4,9,10-tetracarboxdiimide (B, 5.4 g, 6.4 mmol), 2,3-difluorophenol (5.0 g, 38.4 mmol) and K$_2$CO$_3$ (5.7 g, 41.6 mmol) in NMP (100 mL) was stirred at 110° C. under nitrogen for 5 h. Then, the contents of the flask were poured into acetic acid. After 2 minutes, 2 N aqueous HCl was added and stirred for 10 minutes and the precipitated solid was filtered, washed neutral with warm water and vacuum dried at 60° C. The residue was coated on silica gel and purified by column chromatography (SiO$_2$, eluent: DCM/Heptane 1/1). The compound was purified again by two recrystallizations from methanol then from a DCM/heptanes mixture (3×). The red solid collected was washed with warm heptane and dried under vacuum. Pure compound 65 (2.1 g, 27% yield) was obtained as a red solid. $^{19}$F-NMR (282 MHz, in CDCl$_3$): δ=−154 ppm and δ=−135 ppm. Mass (TOF-ESI, m/z): Calculated for C$_{72}$H$_{51}$F$_8$N$_2$O$_8{}^+$ ([M-H]$^+$): 1223.36. Found: 1223.29. $\lambda_{max}$ (ethyl acetate)=548 nm, ε=53400. λ (em) (ethyl acetate) 576 nm.

Molecule 65 is depicted in FIG. 2C. As can be seen form this figure, at least two selected from G2, G3, G4, and G5 at least comprise X, wherein independently at least one of D, E, I, L and M of at least two of said at least two selected from G2, G3, G4, and G5 comprise a group selected from fluorine and chlorine. Here, G2, G3, G4 and G5 comprise X, with each of these four comprise a fluorine (in fact each comprise two fluorine substituents). Note that not necessarily all four of G2, G3, G4 and G5 comprise identical groups.

Synthesis of N,N'-Bis(2,6-diisopropylphenyl)-1,6,7,12-tetra(2,6-difluorophenoxy) perylene-3,4,9,10-tetracarboxdiimide 71. See scheme 1

A mixture of N,N'-Bis-(2,6-diisopropylphenyl)-1,6,7,12-tetrachloroperylene-3,4,9,10-tetracarboxdiimide (B, 4.2 g, 5.0 mmol), 2,6-difluorophenol (5.0 g, 38.4 mmol) and K$_2$CO$_3$ (5.3 g, 38.4 mmol) in NMP (80 mL) was stirred at 110° C. under nitrogen overnight. Then, the contents of the flask were poured into a cold 20% acetic acid solution in water. After 5 minutes, 2 N aqueous HCl was added and stirred for 10 minutes and the precipitated solid was filtered, washed neutral with warm water and vacuum dried at 60° C. The residue was coated on silica gel and purified by column chromatography (SiO$_2$, eluent: DCM/Heptane 2/1). The compound was purified again by a recrystallization from methanol then from a DCM/heptanes mixture (3×). The red solid collected was washed with hot heptane and dried under vacuum. Compound 71 (3.5 g) was obtained as a red solid. $^{19}$F-NMR (282 MHz, in CDCl$_3$): δ=−126 ppm. Mass (TOF-ESI, m/z): Calculated for C$_{72}$H$_{51}$F$_8$N$_2$O$_8{}^+$ ([M-H]$^+$): 1223.36. Found: 1223.86. $\lambda_{max}$ (ethyl acetate)=556 nm, ε=60460. λ (em) (ethyl acetate) 576 nm. Compound 71 is depicted as compound X1 in FIG. 2I.

Synthesis of N,N'-Bis(2,6-diisopropylphenyl)-1,6,7,12-tetra(2,5-dichlorophenoxy) perylene-3,4,9,10-tetracarboxdiimide 72. See scheme 1

A mixture of N,N'-Bis-(2,6-diisopropylphenyl)-1,6,7,12-tetrachloroperylene-3,4,9,10-tetracarboxdiimide (B, 4.0 g, 4.7 mmol), 2,5-dichlorophenol (5.0 g, 30.5 mmol) and K$_2$CO$_3$ (4.3 g, 31.0 mmol) in NMP (80 mL) was stirred at 110° C. under nitrogen overnight. Then, the contents of the flask were poured into a cold 20% acetic acid solution in water. After 5 minutes, 2 N aqueous HCl was added and stirred for 10 minutes and the precipitated solid was filtered, washed neutral with warm water and vacuum dried at 60° C. The residue was coated on silica gel and purified by column chromatography (SiO$_2$, eluent: DCM/Heptane 1/1 to 2/1). The compound was purified again by a recrystallization from a DCM/heptanes mixture (3×). The red solid collected was washed with hot heptane and dried under vacuum. Compound 72 (1.5 g) was obtained as a red solid. Mass (TOF-ESI, m/z): Calculated for C$_{72}$H$_{51}$Cl$_8$N$_2$O$_8{}^+$ ([M-H]$^+$): 1355.11 (100%). Found: 1355.36 (100%). $\lambda_{max}$ (ethyl acetate)=550 nm, ε=47430. λ (em) (ethyl acetate) 576 nm. Compound 72 is depicted as compound X2 in FIG. 2J.

Synthesis of 68

See Scheme 2

1,7,-dibromoperylene-3,4,9,10-tetracarboxylic dianhydride D, Perylene-3,4,9,10-tetracarboxylic dianhydride C (40.0 g, 101.9 mmol), iodine (1.0 g, 4.0 mmol) and sulphuric acid (96%, 470 mL) was premixed and stirred for 2 h at room temperature. The reaction temperature was set to 80° C. and bromine (15.5, 301.7 mmol) was added dropwise. The mixture was reacted further at 80° C. for 20 h. The reaction mixture was cooled to room temperature and the excess Br$_2$ was displaced by nitrogen. The product was precipitated by addition of ice-water and collected by filtration. The precipitate was washed with water several times until the aqueous layer became neutral. Drying in the oven at 60° C. for 3 days gave crude product used for the next step without further purification.

N,N'-Bis-(2,6-diisopropylphenyl)-1,7,-dibromoperylene-3,4,9,10-tetracarboxdiimide E. A mixture of 1,7,-dibromoperylene-3,4,9,10-tetracarboxylic dianhydride D (see above), 2,6-diisopropylaniline (41.5 mL, 220 mmol) in propionic acid (1 L) and NMP (500 mL) was refluxed for 2.5 days under nitrogen. The mixture was cooled to RT and the product was precipitated by addition of water and collected by filtration. The precipitate was washed with water several times until neutral and dried. The product was first purified by column chromatography (SiO$_2$, eluent: DCM/Heptane 2/1 to DCM) to obtain a mixture of the isomeric diimides. The mixture was washed with EtOH (300 mL) and toluene (300 mL) and then heated at 80° C. in toluene (300 mL) over night. The diimide 2386 was recrystallized from the hot toluene solution. The solid was collected through hot filtration and dried under vacuum to give compound 3 (18 g, 20% yield) as an orange powder.

N,N'-Bis(2,6-diisopropylphenyl)-1,7-bis(2,3-difluorophenoxy) perylene-3,4,9,10-tetracarboxdiimide 68

A mixture of N,N'-Bis-(2,6-diisopropylphenyl)-1,7,-dibromoperylene-3,4,9,10-tetracarboxdiimide (E, 1.5 g, 1.7 mmol), 2,3-difluorophenol (675 mg, 5.2 mmol) and $K_2CO_3$ (956 mg, 6.9 mmol) in NMP (70 mL) was stirred at 110° C. under nitrogen for 5 h. Then, the contents of the flask were poured into acetic acid. After 2 minutes, 2 N aqueous HCl was added and stirred for 10 minutes and the precipitated solid was filtered, washed neutral with warm water and vacuum dried at 60° C. The residue was coated on silica gel and purified by column chromatography ($SiO_2$, eluent: DCM/Heptane 1/1). The compound purified again by two recrystallization from a DCM/heptanes mixture (3×). The red solid collected was washed with warm heptane and dried under vacuum. Pure compound 68 (770 mg, 47% yield) was obtained as a red solid. $^{19}$F-NMR (282 MHz, in $CDCl_3$): δ=−155 ppm and δ=−134 ppm. Mass (TOF-ESI, m/z): Calculated for $C_{72}H_{51}F_8N_2O_8^+$ ([M-H]$^+$): 967.33. Found: 967.30. $\lambda_{max}$ (ethyl acetate)=528 nm, ϵ=57200. λ (em) (ethyl acetate) 550 nm.

Molecule 68 is depicted in FIG. 2A. As can be seen form this figure, at least two selected from G2, G3, G4, and G5 at least comprise X, wherein independently at least one of D, E, I, L and M of at least two of said at least two selected from G2, G3, G4, and G5 comprise a group selected from fluorine and chlorine. Here, G2 and G5 comprise X, with each of these two comprise a fluorine (in fact each comprise two fluorine substituents).

Lamps

Example with TLED

A TLED was produced using two different systems, both with CT 4000K and CRI=80:
YAG:Ce+F305 (commercially available organic phosphor) Conversion efficiency=220Lm//Wblue (conversion efficiency=Wblue=amount of lumens generated by conversion of blue light/total power of blue light used)
LuAG:Ce (Lu3Al5O12:Ce) molecule 17 Conversion efficiency=237Lm/Wblue form blue
Hence, the gain is 8%.

Example with Bulb

A bulb was produced using two different systems, both with CCT=2800 CRI 80:
YAG:Ce+F305 Conversion efficiency=185Lm/W form blue
LuAG:Ce molecule 17 Conversion efficiency=230Lm/W form blue
Hence, the gain 24%

Further Examples with a Narrow Band Green Emitter

Another series of combinations of luminescent materials and light source was modeled, which were all tuned at CCT 4000K. The combinations of the emission of a blue LED at 450 nm together with the emission of europium doped Strontium thiogallate ($SrGa_2S_4$:Eu) and the emission of the below indicated organic luminescent materials were evaluated:

| Material | CCT | CRI | Conversion efficiency | Fraction below 645 nm |
|---|---|---|---|---|
| 2 | 4000 K | 86 | 248 | 0.65 |
| X1 = 71 | 4000 K | 85 | 258 | 0.71 |
| X2 = 72 | 4000 K | 81 | 271 | 0.76 |
| 68 | 4000 K | 78 | 287 | 0.87 |
| 17 | 4000 K | 79 | 277 | 0.8 |

From these date it appears that X1, X2 and 68 are either better in CRI, or conversion efficiency or fraction below 645 nm than material 2. For instance, the CRI for 68 is lower, but both conversion efficiency and cutoff are better. For X2, the CRI is slightly better.

Stability Test

Molecules described above tend to degrade under illumination by light used to excite them. We have found that their lifetime can be considerably increased once placed in a aromatic polyester matrix such as polyethylene terephthalate (PET). It was found that the lifetime of the luminescent molecules could be improved by up to a factor of ten as compared to polymer matrices such as polystyrene, polycarbonate and polymethylmethacrylate. We have found that the degradation of the molecules as a function of time can be described by an exponential decay function. In the table below the exponent showing the rate of decay (rate of degradation) under blue illumination at constant intensity (4 W/cm$^2$) indicates the degradation:

| Material | Rate (s−1) |
|---|---|
| PS | $5 \cdot 10^{-7}$ |
| PC | $1 \cdot 10^{-7}$ |
| PMMA | $3 \cdot 10^{-7}$ |
| PET | $3 \cdot 10^{-8}$ |

The invention claimed is:
1. A lighting device comprising (a) a light source configured to generate light source light, and (b) a light converter configured to convert at least part of the light source light into visible converter light, wherein the light converter comprises a matrix containing an organic luminescent material as defined by formula (I):

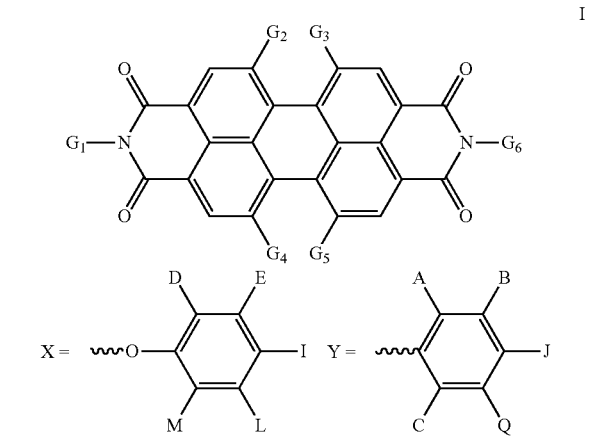

in which:

G₁ and G₆ independently comprise a group selected from a linear alkyl, a branched alkyl, an oxygen-containing alkyl, a cycloalkyl, a naphtyl, and Y;

wherein each of A, B, C, J and Q independently comprise a group selected from hydrogen, fluorine, chlorine, isopropyl, t-butyl, methoxy, an alkyl with up to 16 carbon atoms, and an oxygen containing alkyl with up to 16 carbon atoms, G₂, G₃, G₄ and G₅ independently comprise a group selected from hydrogen, fluorine, chorine, isopropyl, t-butyl, methoxy, alkyl with up to 16 carbon atoms, and oxygen-containing alkyl with up to 16 carbon atoms, and X;

wherein each of D, E, I, L and M independently comprise a group selected from hydrogen, fluorine, chlorine, isopropyl, t-butyl, methoxy, alkyl with up to 16 carbon atoms, and an oxygen-containing alkyl with up to 16 carbon atoms;

and in which at least two selected from G2, G3, G4, and G5 at least comprise X, wherein independently at least two of D, E, I, L and M comprise groups selected from fluorine and chlorine.

2. The lighting device according to claim 1, wherein two of the groups G2, G3, G4 and G5 are hydrogen and wherein the two X comprising groups are identical.

3. The lighting device according to claim 1, wherein G2=G5=X, with D=E=F and I=L=M=hydrogen, and wherein G1=G6=Y, with A=C=isopropyl and B=J=Q=hydrogen.

4. The lighting device according to claim 1, wherein G2=G3=G4=G5 are X, with at least one of A or B is a fluorine or chlorine, and wherein C, J, Q are independently selected from F, Cl, or H.

5. The lighting device according to claim 1, wherein the lighting device further comprises an inorganic luminescent material configured to convert at least part of the light source light into at least green light, wherein the organic luminescent material is configured to provide at least red light, and wherein the light source is configured to provide blue light.

6. The lighting device according to claim 5, wherein the inorganic luminescent material comprises a quantum dot based luminescent material, and wherein the inorganic luminescent material is embedded in the matrix.

7. The lighting device according to claim 1, wherein the matrix comprises polyethylene terephthalate (PET).

8. The lighting device according to claim 1, comprising one or more organic luminescent materials selected from the group consisting of:

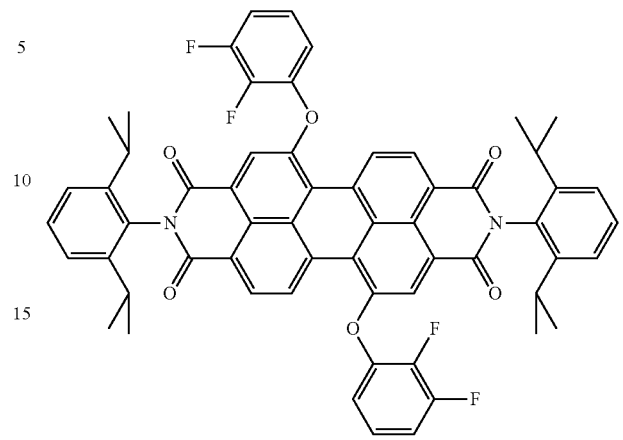

(68)

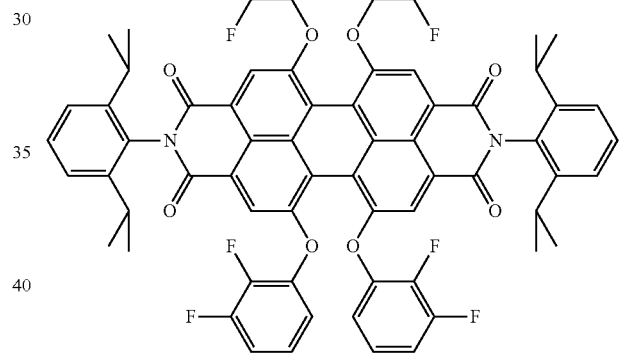

(65)

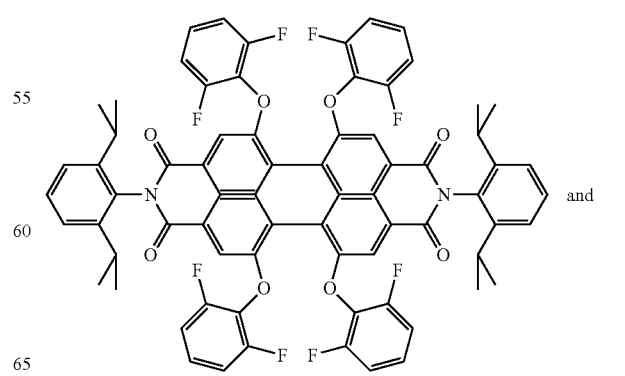

(X1)

and

-continued

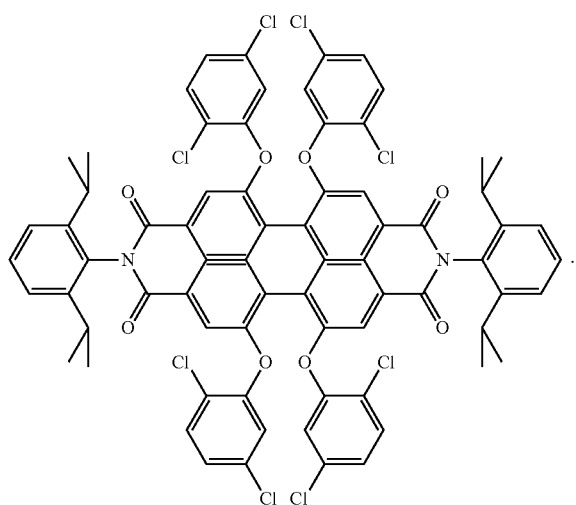

(X2)

9. A light converter comprising a matrix containing an organic luminescent material as defined by formula (I):

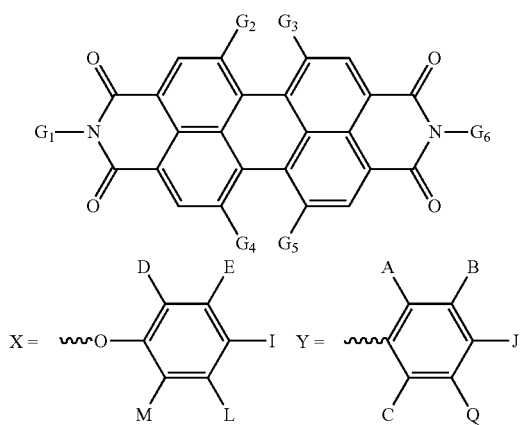

I in which:

G₁ and G₆ independently comprise a group selected from a linear alkyl, a branched alkyl, an oxygen-containing alkyl, a cycloalkyl, a naphtyl, and Y;

wherein each of A, B, C, J and Q independently comprise a group selected from hydrogen, fluorine, chlorine, isopropyl, t-butyl, methoxy, an alkyl with up to 16 carbon atoms, and an oxygen containing alkyl with up to 16 carbon atoms, $G_2$, $G_3$, $G_4$ and $G_5$ independently comprise a group selected from hydrogen, fluorine, chorine, isopropyl, t-butyl, methoxy, alkyl with up to 16 carbon atoms, and oxygen-containing alkyl with up to 16 carbon atoms, and X;

wherein each of D, E, I, L and M independently comprise a group selected from hydrogen, fluorine, chlorine, isopropyl, t-butyl, methoxy, alkyl with up to 16 carbon atoms, and an oxygen-containing alkyl with up to 16 carbon atoms;

and in which at least two selected from G2, G3, G4, and G5 at least comprise X, wherein independently at least two of D, E, I, L and M comprise groups selected from fluorine and chlorine.

10. The light converter according to claim 9, wherein two of the groups G2, G3, G4 and G5 are hydrogen and wherein the two X comprising groups are identical, wherein the light converter further comprises an inorganic luminescent material configured to provide at least green light, wherein the inorganic luminescent material comprises a quantum dot based luminescent material, and wherein the matrix comprises polyethylene terephthalate (PET).

11. The light converter according to claim 9, wherein G2=G5=X, with D=E=F and I=L=M=hydrogen, and wherein G1=G6=Y, with A=C=isopropyl and B=J=Q=hydrogen.

12. The light converter according to claim 9, wherein the matrix comprises polyethylene terephthalate (PET).

* * * * *